US008198420B2

(12) United States Patent
Beau et al.

(10) Patent No.: US 8,198,420 B2
(45) Date of Patent: Jun. 12, 2012

(54) SYNTHETIC COMPOUNDS USEFUL AS NODULATION AGENTS OF LEGUMINOUS PLANTS AND PREPARATION PROCESSES THEREOF

(75) Inventors: Jean-Marie Beau, Menestrau en Villette (FR); Jean Denarie, Castanet Toloson (FR); Alfred Grenier, Saint-Cyr au Mont D'or (FR); Nathalie Grenouillat, Gif-sur-Yvette (FR); Fabienne Maillet, Pompertuzat (FR); Boris Vauzeilles, Paris (FR)

(73) Assignees: Bayer SAS (FR); Institute National de la Recherche Agronomique (FR); Centre National de la Recherche Scientifique (FR)

( * ) Notice: Subject to any disclaimer, the term of this patent is extended or adjusted under 35 U.S.C. 154(b) by 0 days.

(21) Appl. No.: 13/193,505

(22) Filed: Jul. 28, 2011

(65) Prior Publication Data
US 2011/0281729 A1 Nov. 17, 2011

Related U.S. Application Data

(62) Division of application No. 12/587,060, filed on Sep. 30, 2009, now Pat. No. 8,013,132, which is a division of application No. 10/583,567, filed as application No. PCT/EP2004/014909 on Dec. 22, 2004, now Pat. No. 7,619,076.

(30) Foreign Application Priority Data

Dec. 30, 2003 (FR) ...................... 03 15543

(51) Int. Cl.
| | |
|---|---|
| C08B 37/08 | (2006.01) |
| C08B 37/00 | (2006.01) |
| C07H 3/00 | (2006.01) |
| C07H 5/04 | (2006.01) |
| C07H 5/06 | (2006.01) |
| C07H 1/00 | (2006.01) |
| C12P 19/04 | (2006.01) |
| A01N 43/04 | (2006.01) |
| A61K 31/70 | (2006.01) |
| C05D 9/02 | (2006.01) |
| C05F 11/08 | (2006.01) |

(52) U.S. Cl. ........ 536/20; 536/55.2; 536/123.1; 514/25; 514/62; 71/1; 71/7

(58) Field of Classification Search .................... 536/20, 536/55.2, 123.1; 514/25, 62; 71/1, 7
See application file for complete search history.

(56) References Cited

OTHER PUBLICATIONS

Robina, I. et al. "Fatty Acylamino-Trisaccharides. Synthesis and Some Stereochemical Properties", *Tetrahedron*, 52(32), 10771-10784, (1996), ISSN 0040-4020, XP002294810.

Robina, et al. "Synthesis and Conformational Analysis of a Lipotetrasaccharide Related to the Nodulation Factor of Rhizobium Bacteria", *Tetrahedron: Asymmetry*, Elsevier Science Publishers, Amsterdam, NL, vol. 8, No. 8, (Apr. 24, 1997), pp. 1207-1224, ISSN: 0957-4166, XP004059913.

Cardena, Luis et al., "Isolation Chemical Structures and Biological Activity of the Lipo-Chitin Oligosaccharide Nodulation Signals From *Rhizobium etli*", Plant Moleuclar Biology, 29(3), 453-64, ISSN: 0167-4412, (1995), XP009035996.

Grenouillat, N. et al,"Simple Synthesis of Nodulation-Factor Analogues Exhibiting High Affinity Towards a Specific Binding Protein", Angewandte Chemie International Edition, vol. 43, No. 35, p. 4644-4646, (2004).

*Primary Examiner* — Scarlett Goon
(74) *Attorney, Agent, or Firm* — Ostrolenk Faber LLP

(57) ABSTRACT

The present invention relates to synthetic compounds that are active on plants, especially as legume nodulation factors, and also as plant growth stimulators, and to methods for preparing such compounds, which are of formula (I).

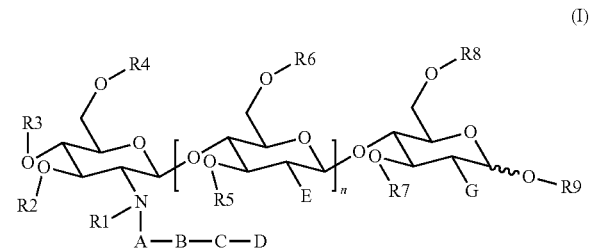

32 Claims, 5 Drawing Sheets

A: 11; B: 3; Control: no LCO

A: 11; B: 3; C: 4; Control: no LCO

A: 3 to $10^{-7}$M; B: 4 to $10^{-7}$M; C: 5 to $10^{-7}$M; D: 11 to $10^{-7}$M; E: 11 to $10^{-9}$M; Control: no LCO A: <u>3</u>; B: <u>9</u>; C: <u>8</u>; D: <u>7</u>; E: <u>6</u>; Control: no LCO A: 3; B: 12; Control: no LCO

SYNTHETIC COMPOUNDS USEFUL AS NODULATION AGENTS OF LEGUMINOUS PLANTS AND PREPARATION PROCESSES THEREOF

CROSS-REFERENCE TO RELATED APPLICATION(S)

This application is a divisional application of Ser. No. 12/587,060 filed on Sep. 30, 2009, which in turn, is a divisional application of U.S. application Ser. No. 10/583,567 filed on Jun. 19, 2006, which is a 35 U.S.C. §371 national phase conversion of PCT/EP2004/014909, filed on Dec. 22, 2004, which claims priority to French Application No. 0315543, filed on Dec. 30, 2003, the entire contents of which are hereby incorporated by reference.

BACKGROUND OF THE INVENTION

The present invention relates to synthetic compounds that are active on plants, especially as legume nodulation factors, and also as plant growth stimulators, and to methods for preparing such compounds.

It is known that the process of nitrogen fixing by legumes is based on symbiosis between these plants and soil bacteria, the *Rhizobia*. The *Rhizobium*-legume symbiosis produces each year, by means of the root nodules, more ammonium than all of the nitrogen fertilizer industry. This symbiosis thus plays a considerable agronomic role. Legumes are very rich in proteins and produce about one third of the plant proteins consumed worldwide, by virtue of pulses such as soybean, pea, horse bean, groundnut, bean and lupin, and forage plants such as alfalfa and clover.

The formation of nitrogen-fixing nodules starts with an exchange of molecular signals, flavonoids secreted by the plant and nodulation factors (Nod factors) synthesized by the bacterium. These factors consist of an oligosaccharide fragment and a lipid chain attached to this skeleton on the non-reducing end. They have structural attributes (substitutions on the sugars at the two ends and variability of the chain) that make them specific to the legume-bacterium couple.

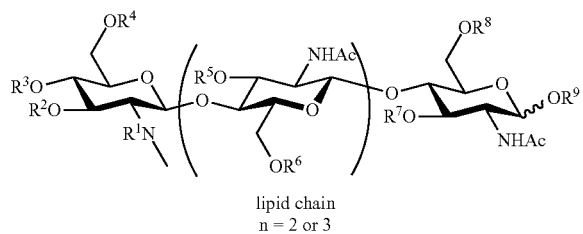

lipid chain
n = 2 or 3

These lipochito-oligosaccharides (LCO) may be either isolated directly from a particular culture of *rhizobia*, synthesized chemically, or obtained chemo-enzymatically. Via the latter method, the oligosaccharide skeleton may be formed by culturing of recombinant *Escherichia coli* bacterial strains in a fermenter, and the lipid chain may then be attached chemically.

Treatment of the seeds of legumes, for instance soybean, with Nod factors at very low concentrations, may result in a large increase in the number of nitrogen-fixing root nodules and a significant increase in the yields, under agronomic conditions. It is thus clear that, in the future, compounds of Nod factor type will be produced industrially for large-scale agronomic use. However, the industrial preparation and conditioning of natural Nod factors presents two types of drawback: (1) the natural Nod factors are difficult to assay via simple methods such as spectrometric methods; (2) they are unstable in the presence of plants or in soils, in particular because they have a —CO—NH— bond that may be broken by plant or microbial enzymes present in the rhizosphere.

BRIEF SUMMARY OF THE INVENTION

One of the aspects of the present invention is to propose a process for preparing compounds of Nod factor type, some of these compounds constituting another aspect of the invention. Specifically, certain biologically active compounds show strong absorption in the ultraviolet range, which makes them easy to assay during their industrial preparation and allows them to be detected and assayed is easily in the product intended for marketing, and allows their stability and storage in such products to be tested. In addition, some of these synthesized compounds show higher stability than the natural Nod factors.

The compounds described may be used to treat plants or plant parts. The term "plants" means wild plants and also crop plants (including future crop plants). The crop plants may be derived either from conventional variety-selection methods, from genetic engineering methods, or from a combination of these two methods. The term "plant parts" means all the aerial or subterranean plant parts or organs, such as flowering-plant seed, root, tuber, rhizome, germ, stalk, leaf and flower. Also included in the category of plant parts are the harvest products and also the reproductive vegetative or germinative material, such as rhizome, tuber, seed, bud or graft.

The compounds described may be used to treat plants or plant parts directly or via the action of their environment or of their culture or storage medium. The usual treatment methods are, for example, dipping, vaporization, evaporation, spraying, spread and application, and for the reproductive material, in particular for the seeds, simple or multilayer coating.

DETAILED DESCRIPTION OF THE INVENTION

Figure 1:
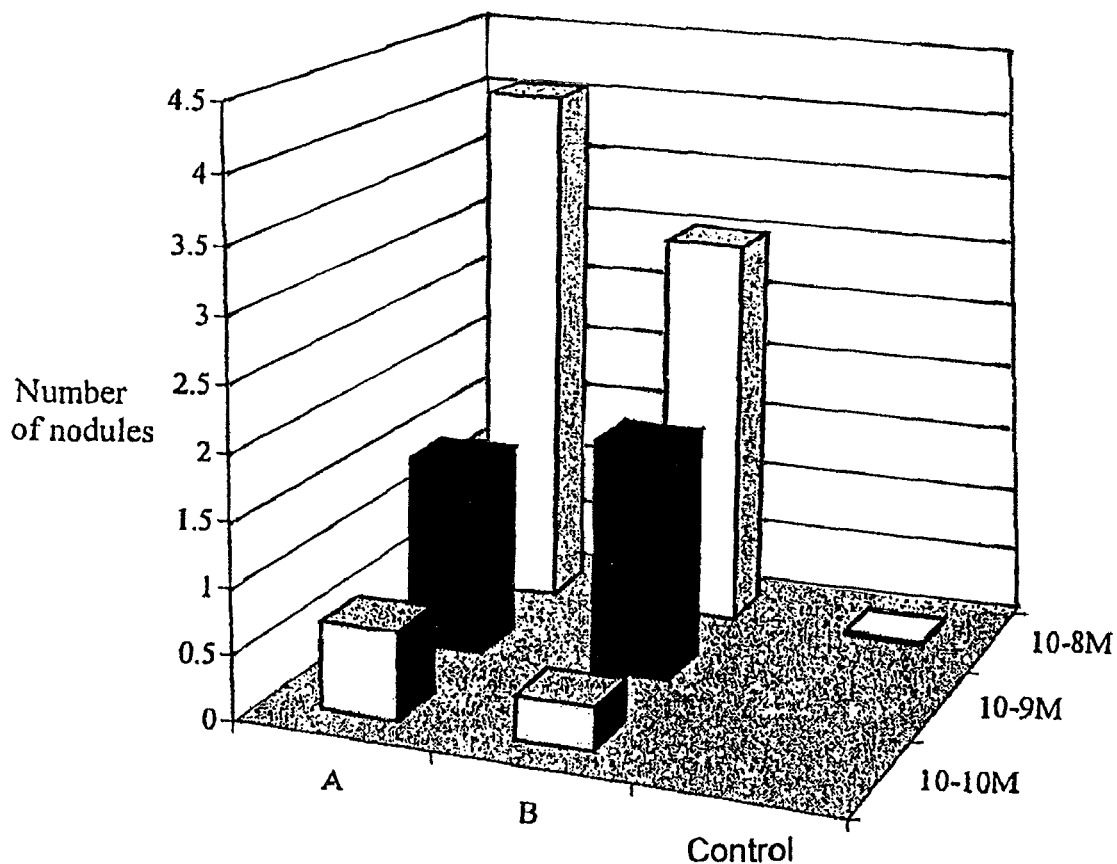
FIG. 1 illustrates the activity of the benzamide derivative 3 meta-substituted with the undec-4Z-enyloxy chain.

In the case of treating the reproductive material, especially seeds, the compounds described may be applied alone or in combination with other active molecules such as fungicides, insecticides, acaricides, nematicides, growth regulators and herbicides. The compounds described and their combinations with active molecules belonging to the abovementioned families may be applied directly or using a suitable formulation. This formulation may be diluted or film-forming agents may be added thereto before use. The use may take place at any of the steps of handling of the seeds between harvesting and sowing, including during self-seeding. Suitable formulations and processes for treating seeds are known to those skilled in the art and are described, inter alia, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The formulations usually used may be solutions, emulsions, suspensions, powders, spraying powders, pastes, soluble pastes, gels, granules, concentrated suspo-emulsions, natural or synthetic impregnated materials, and also microencapsulation using polymers. These formulations are commonly prepared, for example, by mixing the compounds described and/or combinations thereof with other active molecules with solid or liquid formulation supports, using, where appropriate, emulsifying and/or dispersing and/or foaming surfactants. They may also contain a dye such as mineral pigments.

The target Nod factor is especially the factor associated with alfalfa (1) as described above. Among all the existing legumes, alfalfa and vetch have been the subject of numerous studies. By virtue of several activity tests performed with various Nod factor analogs, it has been possible to establish a relationship between the structure of the LCO and the plant response. The isolated nodulation factor that is most active on alfalfa is a tetramer sulfated in position 6 of the reducing sugar, acetylated in position 6 of the sugar located at the nonreducing end and acylated with a chain of 16 carbons containing two unsaturations (C16:2Δ2E,9Z) (1)

in which
n represents 1, 2 or 3;
A represents a substituent chosen from —C(O)—, —C(S)—, —CH$_2$—, —CHR$^{10}$—, —CR$^{10}$R$^{11}$—, —C(O)O—, —C(O)S—, —C(S)O—, —C(S)S—, —C(O)NH—, —C(NH)NH— and —C(S)NH—;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings of 5 or 6 atoms each;
a divalent radical derived from 2 fused aromatic or heteroaromatic rings of 5 or 6 atoms each, comprising 1 or 2 hetero atoms chosen from nitrogen, oxygen and sulfur;
a biphenylene;

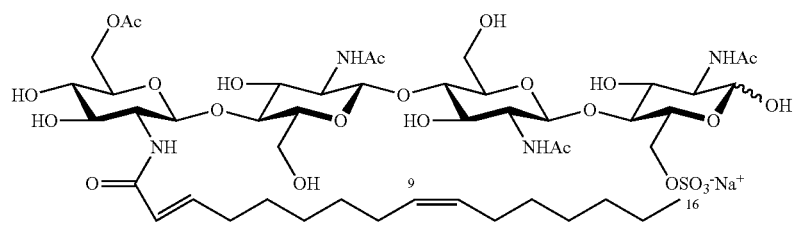

1

It has been shown that the absence of acetate, the addition of a glucosamine unit, or the loss of one of the two unsaturations produce only a moderate reduction in activity. A test of variation of the chain length revealed maximum activity for a chain of 16 carbons. Finally, the sulfate is of prime importance for recognition of the Nod factor by alfalfa, but, on the other hand, its absence is necessary for action in vetch.

Studies have shown that the conjugated unsaturation present at 2 of the lipid chain was important for nodulation, since an analog acylated with a C16:1Δ9Z chain is less active (by just under a factor of 10).

From these results, a series of analogs for which the conjugated amide bond is mimicked by a benzamide bond have been prepared. These compounds constitute one of the aspects of the present invention. Another series of analogs containing a function of benzylamine type constitute another aspect of the invention.

Such compounds are capable of causing or promoting the phenomenon of nodulation in legumes and of stimulating plant growth and development.

The compounds that are plant nodulation factors according to the invention are preferably compounds of formula (I)

(I)

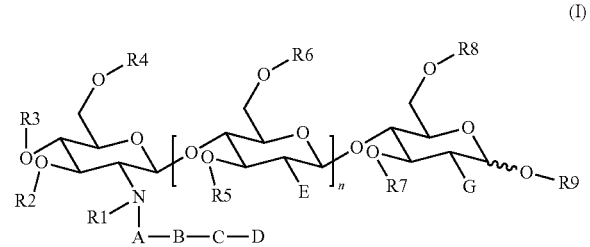

or a heterobiphenylene comprising 1 or 2 hetero atoms chosen from nitrogen, oxygen and sulfur;
these groups possibly being substituted with one or two substituents R$^{12}$ and R$^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;
C represents a substituent chosen from —O—, —S—, —CH$_2$—, —CHR$^{17}$—, —CR$^{17}$R$^{18}$— and —NR$^{19}$;
D represents a linear or branched, saturated or unsaturated hydrocarbon-based chain containing from 2 to 20 carbon atoms;
E and G represent, independently of each other, a substituent chosen from H, OH, OR$^{20}$, NH$_2$ and NHR$^{20}$;
R$^1$ represents a substituent chosen from H, C$_{1-6}$-alkyl, C(O)H and C(O)CH$_3$;
R$^2$, R$^3$, R$^6$, R$^{14}$, R$^{15}$, R$^{16}$ and R$^{19}$ represent, independently of each other, a substituent chosen from H, C$_{1-6}$-alkyl, C(O)C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;
R$^4$ represents a substituent chosen from H, C$_{1-6}$-alkyl and R$^{21}$;
R$^5$ represents a substituent chosen from H, C$_{1-6}$-alkyl, fucosyl and R$^{22}$;
R$^7$ represents a substituent chosen from H, C$_{1-6}$-alkyl, arabinosyl and R$^{23}$;
R$^8$ represents a substituent chosen from H, C$_{1-6}$-alkyl, fucosyl, methylfucosyl, sulfofucosyl, acetylfucosyl, arabinosyl, SO$_3$H, SO$_3$Li, SO$_3$Na, SO$_3$K, SO$_3$N(C$_{1-8}$ alkyl)$_4$ and R$^{24}$;
R$^9$ represents a substituent chosen from H, C$_{1-6}$-alkyl, mannose, glycerol and R$^{25}$;
R$^{10}$, R$^{11}$, R$^{17}$ and R$^{18}$ represent, independently of each other, a substituent chosen from C$_{1-6}$-alkyl and F;

$R^{20}, R^{21}, R^{22}, R^{23}, R^{24}$ and $R^{25}$ represent, independently of each other, a substituent chosen from $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts.

Preferably, the compounds of formula (I) have one or other of the following characteristics, taken separately or in combination:

n represents 2 or 3;
A represents $-C(O)-$ or $-CH_2-$;
B represents a phenylene;
C represents $-O-$;
D represents a linear, saturated or unsaturated hydrocarbon-based chain containing from 3 to 17 carbon atoms;
E and G represent $NHC(O)CH_3$;
$R^1$ represents H, $CH_3$ or $C(O)CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H, SO_3Li, SO_3Na, SO_3K, SO_3N(C_{1-8}$ alkyl)$_4$, fucosyl or methylfucosyl.

Among these compounds, the ones that are preferred are those of formula (I) simultaneously having the following characteristics:

n represents 2 or 3;
A represents $-C(O)-$ or $-CH_2-$;
E and G represent $NHC(O)CH_3$;
$R^1$ represents H, $CH_3$ or $C(O)CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H, SO_3Li, SO_3Na, SO_3K, SO_3N(C_{1-8}$ alkyl)$_4$, fucosyl or methylfucosyl;

even more preferably, those simultaneously having the following characteristics:

n represents 2 or 3;
A represents $-C(O)-$ or $-CH_2-$;
D represents a linear, saturated or unsaturated hydrocarbon-based chain containing from 3 to 17 carbon atoms;
E and G represent $NHC(O)CH_3$;
$R^1$ represents H, $CH_3$ or $C(O)CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H, SO_3Li, SO_3Na, SO_3K, SO_3N(C_{1-8}$ alkyl)$_4$, fucosyl or methylfucosyl;

and most preferably the compounds of formula (I) simultaneously having the following characteristics:

n represents 2 or 3;
A represents $-C(O)-$ or $-CH_2-$;
C represents $-O-$;
D represents a linear, saturated or unsaturated hydrocarbon-based chain containing from 3 to 17 carbon atoms;
E and G represent $NHC(O)CH_3$;
$R^1$ represents H, $CH_3$ or $C(O)CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H, SO_3Li, SO_3Na, SO_3K, SO_3N(C_{1-8}$ alkyl)$_4$, fucosyl or methylfucosyl.

Among these preferred compounds, mention may be made of the compounds of formula (I) simultaneously having the following characteristics:

n represents 2 or 3;
A represents $-C(O)-$ or $-CH_2-$;
B represents a phenylene;
C represents $-O-$;
D represents a linear hydrocarbon-based chain containing 11 carbons, which is saturated, or unsaturated between carbons 4 and 5;
E and G represent $NHC(O)CH_3$;
$R^1$ represents H, $CH_3$ or $C(O)CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H, SO_3Li, SO_3Na, SO_3K, SO_3N(C_{1-8}$ alkyl)$_4$, fucosyl or methylfucosyl.

Among the compounds of the present invention, the compounds for which A represents a carbonyl group are particularly advantageous, and may be represented by formula (Ia):

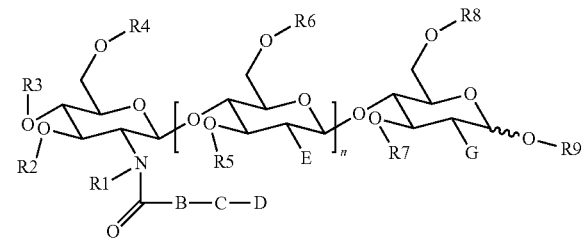

in which
n represents 1, 2 or 3,
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings containing 5 or 6 atoms each;
a divalent radical derived from 2 fused heteroaromatic rings containing 5 or 6 atoms each, and comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, $C(O)OR^{14}$, $C(O)NR^{15}R^{16}$, $CF_3, OCF_3, -NO_2, N_3, OR^{14}, SR^{14}, NR^{15}R^{16}$ and $C_{1-6}$-alkyl;
C represents a substituent chosen from $-O-$, $-S-$, $-CH_2-$, $-CHR^{17}-$, $-CR^{17}R^{18}-$, $-NH-$ and $-NR^{19}$;
D represents a linear or branched, saturated or unsaturated hydrocarbon-based chain containing from 2 to 20 carbon atoms;
E and G represent, independently of each other, a substituent chosen from H, OH, $OR^{20}$, $NH_2$ and $NHR^{20}$;
$R^1$ represents a substituent chosen from H, $C_{1-6}$-alkyl, $C(O)H$ and $C(O)CH_3$;
$R^2, R^3$ and $R^6$ represent, independently of each other, a substituent chosen from H, $C_{1-6}$-alkyl, $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;
$R^4$ represents a substituent chosen from H, $C_{1-6}$-alkyl and $R^{21}$;
$R^5$ represents a substituent chosen from H, $C_{1-6}$-alkyl, fucosyl and $R^{22}$;

$R^7$ represents a substituent chosen from H, $C_{1-6}$-alkyl, arabinosyl and $R^{23}$;

$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}$ alkyl$)_4$ and $R^{24}$;

$R^9$ represents a substituent chosen from H, $C_{1-6}$-alkyl, mannose, glycerol and $R^{25}$;

$R^{10}$, $R^{11}$, $R^{17}$ and $R^{18}$ represent, independently of each other, a substituent chosen from $C_{1-6}$-alkyl and F;

$R^{14}$, $R^{15}$, $R^{16}$ and $R^{19}$ represent, independently of each other, a substituent chosen from H, $C_{1-6}$-alkyl, —C(O)$C_{1-6}$-alkyl, —C(S)$C_{1-6}$-alkyl, —C(O)O$C_{1-6}$-alkyl, —C(O)$NH_2$, —C(S)$NH_2$, —C(NH)$NH_2$, —C(O)NH$C_{1-6}$-alkyl, —C(S)NH$C_{1-6}$-alkyl and —C(NH)NH$C_{1-6}$-alkyl;

$R^{20}$, $R^{21}$, $R^{22}$, $R^{23}$, $R^{24}$ and $R^{25}$ represent, independently of each other, a substituent chosen from C(O)$C_{1-6}$-alkyl, —C(S)$C_{1-6}$-alkyl, —C(O)O$C_{1-6}$-alkyl, —C(O)$NH_2$, —C(S)$NH_2$, —C(NH)$NH_2$, —C(O)NH$C_{1-6}$-alkyl, —C(S)NH$C_{1-6}$-alkyl and —C(NH)NH$C_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium, or tetraalkylammonium salts.

Among these compounds of formula (Ia) the ones that are preferred are those having the following characteristics, taken separately or in combination:

n represents 2 or 3;
B represents a phenylene;
C represents —O—;
D represents a linear, saturated or unsaturated hydrocarbon-based chain containing from 3 to 17 carbon atoms;
E and G represent NHC(O)$CH_3$;
$R^1$ represents H or $CH_3$;
$R^2$, $R^3$, $R^5$, $R^6$, $R^7$ and $R^9$ represent H;
$R^4$ represents H, C(O)$CH_3$ or C(O)$NH_2$;
$R^8$ represents H, $SO_3H$, $SO_3Li$, $SO_3Na$, $SO_3K$, $SO_3N(C_{1-8}$ alkyl$)_4$, fucosyl or methylfucosyl; more preferably, those simultaneously having the following characteristics:
n represents 2 or 3;
E and G represent NHC(O)$CH_3$;
$R^1$ represents H or $CH_3$;
$R^2$, $R^3$, $R^5$, $R^6$, $R^7$ and $R^9$ represent H;
$R^4$ represents H, C(O)$CH_3$ or C(O)$NH_2$;
$R^8$ represents H, $SO_3H$, $SO_3Li$, $SO_3Na$, $SO_3K$, $SO_3N(C_{1-8}$ alkyl$)_4$, fucosyl or methylfucosyl;
even more preferably, those simultaneously having the following characteristics:
n represents 2 or 3;
D represents a linear, saturated or unsaturated hydrocarbon-based chain containing from 3 to 17 carbon atoms;
E and G represent NHC(O)$CH_3$;
$R^1$ represents H or $CH_3$;
$R^2$, $R^3$, $R^5$, $R^6$, $R^7$ and $R^9$ represent H;
$R^4$ represents H, C(O)$CH_3$ or C(O)$NH_2$;
$R^8$ represents H, $SO_3H$, $SO_3Li$, $SO_3Na$, $SO_3K$, $SO_3N(C_{1-8}$ alkyl$)_4$, fucosyl or methylfucosyl.

Among these compounds of formula (Ia), the ones that are more preferred are those simultaneously having the following characteristics:
n represents 2 or 3;
C represents —O—;
D represents a linear, saturated or unsaturated hydrocarbon-based chain containing from 3 to 17 carbon atoms;
E and G represent NHC(O)$CH_3$;
$R^1$ represents H or $CH_3$;
$R^2$, $R^3$, $R^5$, $R^6$, $R^7$ and $R^9$ represent H;
$R^4$ represents H, C(O)$CH_3$ or C(O)$NH_2$;
$R^8$ represents H, $SO_3H$, $SO_3Li$, $SO_3Na$, $SO_3K$, $SO_3N(C_{1-8}$ alkyl$)_4$, fucosyl or methylfucosyl;
or those simultaneously having the following characteristics:
n represents 2 or 3;
B represents a phenylene;
C represents —O—;
D represents a linear hydrocarbon-based chain containing 11 carbons, which is saturated, or unsaturated between carbons 4 and 5;
E and G represent NHC(O)$CH_3$;
$R^1$ represents H or $CH_3$;
$R^2$, $R^3$, $R^5$, $R^6$, $R^7$ and $R^9$ represent H;
$R^4$ represents H, C(O)$CH_3$ or C(O)$NH_2$;
$R^8$ represents H, $SO_3H$, $SO_3Li$, $SO_3Na$, $SO_3K$, $SO_3N(C_{1-8}$ alkyl$)_4$, fucosyl or methylfucosyl.

Among the compounds of the present invention, the compounds for which A represents a methylene group are also particularly advantageous, and may be represented by formula (Ib):

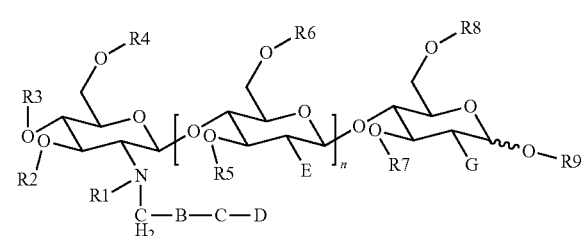

(Ib)

in which
n represents 1, 2 or 3;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings each containing 5 or 6 atoms;
a divalent radical derived from 2 fused aromatic or heteroaromatic rings each containing 5 or 6 atoms, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, C(O)$OR^{14}$, C(O)$NR^{15}R^{16}$, $CF_3$, $OCF_3$, —$NO_2$, $N_3$, $OR^{14}$, $SR^{14}$, $NR^{15}R^{16}$ and $C_{1-6}$-alkyl;
C represents a substituent chosen from —O—, —S—, —$CH_2$—, —$CHR^{17}$—, —$CR^{17}R^{18}$—, —NH— and —$NR^{19}$;

D represents a linear or branched, saturated or unsaturated hydrocarbon-based chain containing from 2 to 20 carbon atoms;

E and G represent, independently of each other, a substituent chosen from H, OH, OR$^{20}$, NH$_2$ and NHR$^{20}$;

R$^1$ represents a substituent chosen from H, C$_{1-6}$-alkyl, C(O)H and C(O)CH$_3$;

R$^2$, R$^3$ and R$^6$ represent, independently of each other, a substituent chosen from H, C$_{1-6}$-alkyl, C(O)C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

R$^4$ represents a substituent chosen from H, C$_{1-6}$-alkyl and R$^{21}$;

R$^5$ represents a substituent chosen from H, C$_{1-6}$-alkyl, fucosyl and R$^{22}$;

R$^7$ represents a substituent chosen from H, C$_{1-6}$-alkyl, arabinosyl and R$^{23}$;

R$^8$ represents a substituent chosen from H, C$_{1-6}$-alkyl, fucosyl, methylfucosyl, sulfofucosyl, acetylfucosyl, arabinosyl, SO$_3$H, SO$_3$Li, SO$_3$Na, SO$_3$K, SO$_3$N(C$_{1-8}$ alkyl)$_4$ and R$^{24}$;

R$^9$ represents a substituent chosen from H, C$_{1-6}$-alkyl, mannose, glycerol and R$^{25}$;

R$^{10}$, R$^{11}$, R$^{17}$ and R$^{18}$ represent, independently of each other, a substituent chosen from C$_{1-6}$-alkyl and F;

R$^{14}$, R$^{15}$, R$^{16}$ and R$^{19}$ represent, independently of each other, a substituent chosen from H, C$_{1-6}$-alkyl, —C(O) C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O) NHC$_{1-6}$-alkyl, —C(S)NHC$_{1-6}$-alkyl and —C(NH) NHC$_{1-6}$-alkyl;

R$^{20}$, R$^{21}$, R$^{22}$, R$^{23}$, R$^{24}$ and R$^{25}$ represent, independently of each other, a substituent chosen from C(O)C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts.

Among these compounds of formula (Ib) the ones that are preferred are those having the following characteristics, taken separately or in combination:
n represents 2 or 3;
B represents a phenylene;
C represents —O—;
D represents a linear, saturated or unsaturated hydrocarbon-based chain containing from 3 to 17 carbon atoms;
E and G represent NHC(O)CH$_3$;
R$^1$ represents H or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl;
more preferably, those simultaneously having the following characteristics:
n represents 2 or 3;
E and G represent NHC(O)CH$_3$;
R$^1$ represents H or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl;

even more preferably, those simultaneously having the following characteristics:
n represents 2 or 3;
D represents a linear, saturated or unsaturated hydrocarbon-based chain containing from 3 to 17 carbon atoms;
E and G represent NHC(O)CH$_3$;
R$^1$ represents H or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl.

Among these compounds of formula (Ib), the ones that are more preferred are those simultaneously having the following characteristics:
n represents 2 or 3;
C represents —O—;
D represents a linear, saturated or unsaturated hydrocarbon-based chain containing from 3 to 17 carbon atoms;
E and G represent NHC(O)CH$_3$;
R$^1$ represents H or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl;
or those simultaneously having the following characteristics:
n represents 2 or 3;
B represents a phenylene;
C represents —O—;
D represents a linear hydrocarbon-based chain containing 11 carbons, which is saturated, or unsaturated between carbons 4 and 5;
E and G represent NHC(O)CH$_3$;
R$^1$ represents H or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$ alkyl)$_4$, fucosyl or methylfucosyl.

Among the compounds of the present invention, the compounds for which C represents an oxygen atom are also particularly advantageous, and may be represented by formula (Ic):

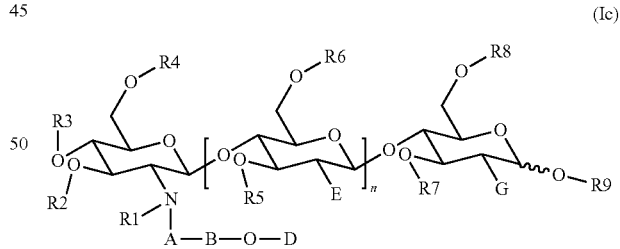

(Ic)

in which
n represents 1, 2 or 3, preferably 2 or 3;
A represents a substituent chosen from —C(O)—, —C(S)—, —CH$_2$—, —CHR$^{10}$—, CR$^{10}$R$^{11}$—, —C(O) O—, —C(O)S—, —C(S)O—, —C(S)S—, —C(O) NH—, —C(NH)NH— and —C(S)NH—, preferably —C(O)—;
B represents
an arylene;
a heteroarylene comprising 1 or 2 hetero atoms chosen from nitrogen, oxygen and sulfur;
a naphthylene;

a heteronaphthylene comprising 1 or 2 hetero atoms chosen from nitrogen, oxygen and sulfur;

a divalent radical derived from 2 fused aromatic rings containing 5 or 6 atoms each;

a divalent radical derived from 2 fused aromatic or heteroaromatic rings containing 5 or 6 atoms each, comprising 1 or 2 hetero atoms chosen from nitrogen, oxygen and sulfur;

a biphenylene;

or a heterobiphenylene comprising 1 or 2 hetero atoms chosen from nitrogen, oxygen and sulfur;

these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, $-NO_2$, $N_3$, $OR^{14}$, $SR^{14}$, $NR^{15}R^{16}$ and $C_{1-6}$-alkyl;

D represents a linear or branched, saturated or unsaturated hydrocarbon-based chain containing from 2 to 20 carbon atoms, preferably a linear hydrocarbon-based chain containing 11 carbons, which is saturated, or unsaturated between carbons 4 and 5;

E and G represent, independently of each other, a substituent chosen from H, OH, $OR^{20}$, $NH_2$ and $NHR^{20}$, preferably $NHC(O)CH_3$;

$R^1$ represents a substituent chosen from H, $C_{1-6}$-alkyl, $C(O)H$ and $C(O)CH_3$, preferably H or $CH_3$;

$R^2$, $R^3$ and $R^6$ represent, independently of each other, a substituent chosen from H, $C_{1-6}$-alkyl, $-C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl; preferably H;

$R^4$ represents a substituent chosen from H, $C_{1-6}$-alkyl and $R^{21}$, preferably H, $C(O)CH_3$ or $C(O)NH_2$;

$R^5$ represents a substituent chosen from H, $C_{1-6}$-alkyl, fucosyl and $R^{22}$, preferably H;

$R^7$ represents a substituent chosen from H, $C_{1-6}$-alkyl, arabinosyl and $R^{23}$, preferably H;

$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}$ alkyl$)_4$ and $R^{24}$, preferably H, $SO_3H$, $SO_3Li$, $SO_3Na$, $SO_3K$, $SO_3N(C_{1-8}$alkyl$)_4$, fucosyl or methylfucosyl;

$R^6$ represents a substituent chosen from H, $C_{1-6}$-alkyl, mannose, glycerol and $R^{25}$, preferably H;

$R^{10}$, $R^{11}$, $R^{17}$ and $R^{18}$ represent, independently of each other, a substituent chosen from $C_{1-6}$-alkyl and F;

$R^{14}$, $R^{15}$, $R^{16}$ and $R^{19}$ represent, independently of each other, a substituent chosen from H, $C_{1-6}$-alkyl, $-C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;

$R^{20}$, $R^{21}$, $R^{22}$, $R^{23}$, $R^{24}$ and $R^{25}$ represent, independently of each other, a substituent chosen from $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts.

Among the compounds of formula (Ic), the ones that are preferred are those having one or other of the following characteristics, taken separately or in combination:

n represents 2 or 3;

A represents $-C(O)-$ or $-CH_2-$;

B represents a phenylene;

D represents a linear, saturated or unsaturated hydrocarbon-based chain containing from 3 to 17 carbon atoms;

E and G represent $NHC(O)CH_3$;

$R^1$ represents H, $CH_3$ or $C(O)CH_3$;

$R^2$, $R^3$, $R^5$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}$ alkyl$)_4$, fucosyl or methylfucosyl;

more preferably, those simultaneously having the following characteristics:

n represents 2 or 3;

A represents $-C(O)-$ or $-CH_2-$;

E and G represent $NHC(O)CH_3$;

$R^1$ represents H, $CH_3$ or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}$ alkyl$)_4$, fucosyl or methylfucosyl;

even more preferably, those simultaneously having the following characteristics:

n represents 2 or 3;

A represents $-C(O)-$ or $-CH_2-$;

D represents a linear, saturated or unsaturated hydrocarbon-based chain containing from 3 to 17 carbon atoms;

E and G represent $NHC(O)CH_3$;

$R^1$ represents H, $CH_3$ or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}$ alkyl$)_4$, fucosyl or methylfucosyl;

most preferably, those simultaneously having the following characteristics:

n represents 2 or 3;

A represents $-C(O)-$ or $-CH_2-$;

B represents a phenylene;

D represents a linear hydrocarbon-based chain containing 11 carbon atoms, which is saturated, or unsaturated between carbons 4 and 5;

E and G represent $NHC(O)CH_3$;

$R^1$ represents H, $CH_3$ or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}$ alkyl$)_4$, fucosyl or methylfucosyl.

Among the compounds of the present invention, the compounds for which A represents a carbonyl group and C rep resents an oxygen atom are most particularly advantageous, and may be represented by formula (Id):

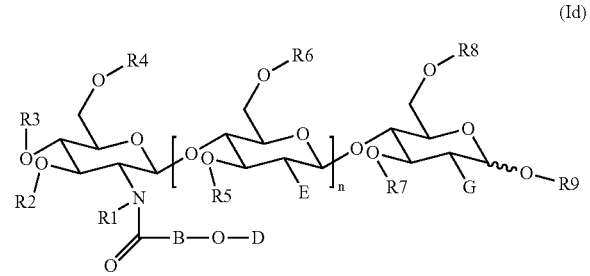

in which
n represents 1, 2 or 3, preferably 2 or 3;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings each containing 5 or 6 atoms;
a divalent radical derived from 2 fused aromatic or heteroaromatic rings each containing 5 or 6 atoms, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, C(O)O$R^{14}$, C(O)N$R^{15}R^{16}$, CF$_3$, OCF$_3$, —NO$_2$, N$_3$, O$R^{14}$, S$R^{14}$, N$R^{15}R^{16}$ and C$_{1-6}$alkyl;
D represents a linear or branched, saturated or unsaturated hydrocarbon-based chain containing from 2 to 20 carbon atoms, preferably a linear hydrocarbon-based chain containing 11 carbon atoms, which is saturated, or unsaturated between carbons 4 and 5;
E and G represent, independently of each other, a substituent chosen from H, OH, O$R^{20}$, NH$_2$ and NH$R^{20}$, preferably NHC(O)CH$_3$;
$R^1$ represents a substituent chosen from H, C$_{1-6}$-alkyl, C(O)H and C(O)CH$_3$, preferably H or CH$_3$;
$R^2$, $R^3$ and $R^6$ represent, independently of each other, a substituent chosen from H, C$_{1-6}$-alkyl, —C(O)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl; preferably H;
$R^4$ represents a substituent chosen from H, C$_{1-6}$-alkyl and $R^{21}$, preferably H, C(O)CH$_3$ or C(O)NH$_2$;
$R^5$ represents a substituent chosen from H, C$_{1-6}$-alkyl, fucosyl and $R^{22}$, preferably H;
$R^7$ represents a substituent chosen from H, C$_{1-6}$-alkyl, arabinosyl and $R^{23}$, preferably H;
$R^8$ represents a substituent chosen from H, C$_{1-6}$-alkyl, fucosyl, methylfucosyl, sulfofucosyl, acetylfucosyl, arabinosyl, SO$_3$H, SO$_3$Li, SO$_3$Na, SO$_3$K, SO$_3$N(C$_{1-8}$ alkyl)$_4$ and $R^{24}$, preferably H, SO$_3$H, SO$_3$Li, SO$_3$Na, SO$_3$K, SO$_3$N(C$_{1-8}$alkyl)$_4$, fucosyl or methylfucosyl;
$R^9$ represents a substituent chosen from H, C$_{1-6}$-alkyl, mannose, glycerol and $R^{25}$, preferably H;

$R^{10}$, $R^{11}$, $R^{17}$ and $R^{18}$ represent, independently of each other, a substituent chosen from C$_{1-6}$-alkyl and F;
$R^{14}$, $R^{15}$, $R^{16}$ and $R^{19}$ represent, independently of each other, a substituent chosen from H, C$_{1-6}$-alkyl, —C(O) C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O) NHC$_{1-6}$-alkyl, —C(S)NHC$_{1-6}$-alkyl and —C(NH) NHC$_{1-6}$-alkyl;
$R^{20}$, $R^{21}$, $R^{22}$, $R^{23}$, $R^{24}$ and $R^{25}$ represent, independently of each other, a substituent chosen from —C(O)C$_{1-6}$-alkyl, —C(S)C$_{1-6}$-alkyl, —C(O)OC$_{1-6}$-alkyl, —C(O)NH$_2$, —C(S)NH$_2$, —C(NF)NH$_2$, —C(O)NHC$_{1-6}$-alkyl, —C(S)NHC$_{1-6}$-alkyl and —C(NH)NHC$_{1-6}$-alkyl;
and also the possible geometrical and/or isomers, enantiomers and/or diastereoisomers, tautomers, salts, N-oxides, sulfoxides, sulfones and metal or metalloid complexes thereof, which are agriculturally acceptable. Among the compounds defined above, the most important compounds are the salts, more particularly the lithium, sodium, potassium or tetraalkylammonium salts.

Among the compounds of formula (Id), the ones that are preferred are those having one or other of the following characteristics, taken separately or in combination;
n represents 2 or 3;
B represents a phenylene;
D represents a linear, saturated or unsaturated hydrocarbon-based chain containing from 3 to 17 carbon atoms;
E and G represent NHC(O)CH$_3$;
$R^1$ represents H or CH$_3$;
$R^2$, $R^3$, $R^5$, $R^6$, $R^7$ and $R^9$ represent H;
$R^4$ represents H, C(O)CH$_3$ or C(O)NH$_2$;
$R^8$ represents H, SO$_3$H, SO$_3$Li, SO$_3$Na, SO$_3$K, SO$_3$N(C$_{1-8}$ alkyl)$_4$, fucosyl or methylfucosyl;
more preferably, those simultaneously having the following characteristics:
n represents 2 or 3;
E and G represent NHC(O)CH$_3$;
$R^1$ represents H or CH$_3$;
$R^2$, $R^3$, $R^5$, $R^6$, $R^7$ and $R^9$ represent H;
$R^4$ represents H, C(O)CH$_3$ or C(O)NH$_2$;
$R^8$ represents H, SO$_3$H, SO$_3$Li, SO$_3$Na, SO$_3$K, SO$_3$N(C$_{1-8}$ alkyl)$_4$, fucosyl or methylfucosyl;
even more preferably, those simultaneously having the following characteristics:
n represents 2 or 3;
D represents a linear, saturated or unsaturated hydrocarbon-based chain containing from 3 to 17 carbon atoms;
E and G represent NHC(O)CH$_3$;
$R^1$ represents H or CH$_3$;
$R^2$, $R^3$, $R^5$, $R^6$, $R^7$ and $R^9$ represent H;
$R^4$ represents H, C(O)CH$_3$ or C(O)NH$_2$;
$R^8$ represents H, SO$_3$H, SO$_3$Li, SO$_3$Na, SO$_3$K, SO$_3$N(C$_{1-8}$ alkyl)$_4$, fucosyl or methylfucosyl;
and most preferably those simultaneously having the following characteristics:
n represents 2 or 3;
B represents a phenylene;
D represents a linear hydrocarbon-based chain containing 11 carbon, which is saturated, or unsaturated between carbons 4 and 5;
E and G represent NHC(O)CH$_3$;
$R^1$ represents H or CH$_3$;
$R^2$, $R^3$, $R^5$, $R^6$, $R^7$ and $R^9$ represent H;
$R^4$ represents H, C(O)CH$_3$ or C(O)NH$_2$;
$R^8$ represents H, SO$_3$Li, SO$_3$Na, SO$_3$K, SO$_3$N(C$_{1-8}$ alkyl)$_4$, fucosyl or methylfucosyl.

Among the compounds of the present invention, the compounds for which A represents a methylene group and C represents an oxygen atom are also most particularly advantageous, and may be represented by formula (Ie):

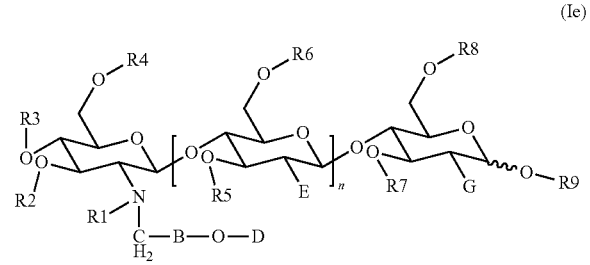

(Ie)

in which
n represents 1, 2 or 3, preferably 2 or 3;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings containing 5 or 6 atoms each;
a divalent radical derived from 2 fused aromatic or heteroaromatic rings containing 5 or 6 atoms each, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, $-NO_2$, $N_3$, $OR^{14}$, $SR^{14}$, $NR^{15}R^{16}$ and $C_{1-6}$-alkyl;
D represents a linear or branched, saturated or unsaturated hydrocarbon-based chain containing from 2 to 20 carbon atoms, preferably a linear hydrocarbon-based chain containing 11 carbons, which is saturated, or unsaturated between carbons 4 and 5;
E and G represent, independently of each other, a substituent chosen from H, OH, $OR^{20}$, $NH_2$ and $NHR^{20}$, preferably $NHC(O)CH_3$;
$R^1$ represents a substituent chosen from H, $C_{1-6}$-alkyl, $C(O)H$ and $C(O)CH_3$, preferably H or $CH_3$;
$R^2$, $R^3$ and $R^6$ represent, independently of each other, a substituent chosen from H, $C_{1-6}$-alkyl, $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl; preferably H;
$R^4$ represents a substituent chosen from H, $C_{1-6}$-alkyl and $R^{21}$, preferably H, $C(O)CH_3$ or $C(O)NH_2$;
$R^5$ represents a substituent chosen from H, $C_{1-6}$-alkyl, fucosyl and $R^{22}$, preferably H;
$R^7$ represents a substituent chosen from H, $C_{1-6}$-alkyl, arabinosyl and $R^{23}$, preferably H;
$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}$-alkyl$)_4$ and $R^{24}$, preferably H, $SO_3H$, $SO_3Li$, $SO_3Na$, $SO_3K$, $SO_3N(C_{1-8}$alkyl$)_4$, fucosyl or methylfucosyl;
$R^9$ represents a substituent chosen from H, $C_{1-6}$-alkyl, mannose, glycerol and $R^{25}$, preferably H;
$R^{10}$, $R^{11}$, $R^{17}$ and $R^{18}$ represent, independently of each other, a substituent chosen from $C_{1-6}$-alkyl and F;
$R^{14}$, $R^{15}$, $R^{16}$ and $R^{19}$ represent, independently of each other, a substituent chosen from H, $C_{1-6}$-alkyl, $-C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;
$R^{20}$, $R^{21}$, $R^{22}$, $R^{23}$, $R^{24}$ and $R^{25}$ represent, independently of each other, a substituent chosen from $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;
and also the possible geometrical and/or optical isomers, enantiomers and/or diastereoisomers, tautomers, salts, N-oxides, sulfoxides, sulfones and metal or metalloid complexes thereof, which are agriculturally acceptable. Among the compounds defined above, the most important compounds are the salts, more particularly the lithium, sodium, potassium or tetraalkylammonium salts.

Among the compounds of (Ie), the ones that are preferred are those having one or other of the following characteristics, taken separately or in combination:
n represents 2 or 3;
B represents a phenylene;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}$alkyl$)_4$, fucosyl or methylfucosyl;
more preferably, those simultaneously having the following characteristics:
n represents 2 or 3;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}$alkyl$)_4$, fucosyl or methylfucosyl;
even more preferably, those simultaneously having the following characteristics:
n represents 2 or 3;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}$alkyl$)_4$, fucosyl or methylfucosyl;
and most preferably those simultaneously having the following characteristics:
n represents 2 or 3;
B represents a phenylene;
D represents a linear hydrocarbon-based chain containing 11 carbons, which is saturated, or unsaturated between carbons 4 and 5;
E and G represent $NHC(O)CH_3$;
$R^1$ represents H or $C(O)CH_3$;
$R^2$, $R^3$, $R^5$, $R^6$, $R^7$ and $R^9$ represent H;

$R^4$ represents H, C(O)CH$_3$ or C(O)NH$_2$;

$R^8$ represents H, SO$_3$H, SO$_3$Li, SO$_3$Na, SO$_3$K, SO$_3$N(C$_{1-8}$ alkyl)$_4$, fucosyl or methylfucosyl.

Among the compounds of formula (I), (Ia), (Ib), (Ic), (Id) or (Ie) according to the invention, the ones that are preferred are those for which:

B represents a substituent chosen from:

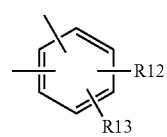
B1

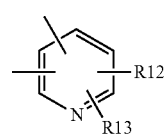
B2

B3

B4

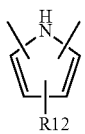
B5

B6

B7

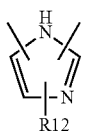
B8

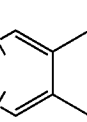
B9

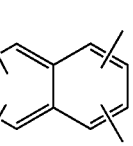
B10

-continued

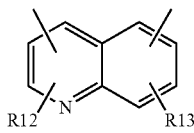
B11

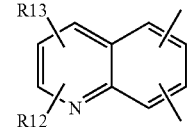
B12

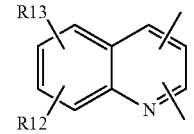
B13

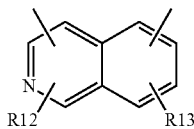
B14

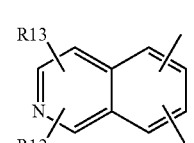
B15

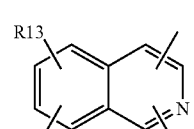
B16

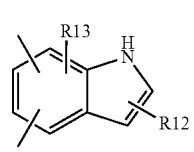
B17

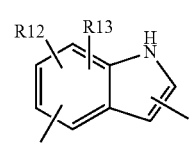
B18

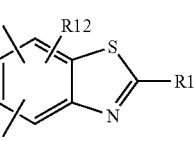
B19

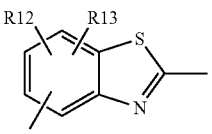
B20 in which $R^{12}$ and $R^{13}$ represent two substituents chosen, independently of each other, from halogen, CN, CF$_3$, OCF$_3$, —NO$_2$, N$_3$, OR$^{14}$, SR$^{14}$, NR$^{15}$R$^{16}$ and C$_{1-6}$-alkyl.

Among the compounds of formula (I), (Ia), (Ib), (Ic), (Id) or (Ie) according to the invention, the ones that are also preferred are those for which B represents
an arylene;

a heteroarylene comprising 1 or 2 hetero atoms chosen from nitrogen, oxygen and sulfur;

a naphthylene;

or a heteronaphthylene comprising 1 or 2 hetero atoms chosen from nitrogen, oxygen and sulfur;

these groups possibly being substituted with one or two substituents $R^{12}$ and $R^{13}$ chosen, independently of each other, from halogen, CN, C(O)OR$^{14}$, C(O)NR$^{15}$R$^{16}$, OCF$_3$, N$_3$, OR$^{14}$, SR$^{14}$, NR$^{15}$R$^{16}$ and C$_{1-6}$-alkyl;

preferably, those for which

B represents an arylene;

or a heteroarylene comprising 1 or 2 hetero atoms chosen from nitrogen, oxygen and sulfur;

these groups possibly being substituted with one or two substituents $R^{12}$ and $R^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;

more preferably, those for which

B represents a phenylene;

or a heterophenylene comprising 1 or 2 hetero atoms chosen from nitrogen, oxygen and sulfur;

these groups possibly being substituted with one or two substituents $R^{12}$ and $R^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;

mention may be made especially of those for which

B represents a phenylene B1 that may be substituted with one or two substituents $R^{12}$ and $R^{13}$ chosen, independently of each other, from halogen, CN, CF$_3$, OCF$_3$, —NO$_2$, N$_3$, OR$^{14}$, SR$^{14}$, NR$^{15}$R$^{16}$ and C$_{1-6}$-alkyl.

Among the preferred compounds of the present invention, mention may also be made of those having one of the following characteristics, taken separately or in combination:

n=2 or 3;

A represents —C(O)— or —CH$_2$—;

C represents —O—;

E and G represent NHC(O)CH$_3$;

$R^1$ represents H or C(O)CH$_3$;

$R^2$, $R^3$, $R^5$, $R^6$ and $R^7$ represent a hydrogen atom;

$R^4$ represents a substituent chosen from H, C(O)CH$_3$ and C(O)NH$_2$;

$R^8$ represents a substituent chosen from H, fucosyl, methylfucosyl, sulfofucosyl, acetylfucosyl, arabinosyl, SO$_3$H, SO$_3$Li, SO$_3$Na, SO$_3$K and SO$_3$N(C$_{1-8}$alkyl)$_4$;

$R^9$ represents a hydrogen atom;

even more preferably, those having the following combination of characteristics:

n=2 or 3;

A represents —C(O)— or —CH$_2$—;

C represents —O—;

D represents a linear, saturated or unsaturated hydrocarbon-based chain containing from 7 to 15 carbon atoms; preferably a hydrocarbon-based chain according to one of the formulae represented below

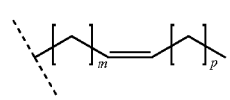
D1

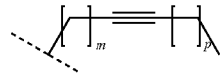
D2

D3

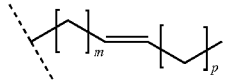
D4

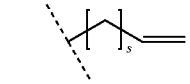
D5

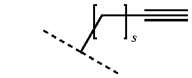
D6 in which m=1 to 12 p=0 to 11 q=6 to 14 s=5 to 13 with m+p$\leq$12 and m+p$\geq$4; even more preferably a hydrocarbon-based chain according to one of the formulae represented below

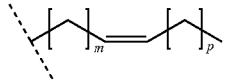
D1

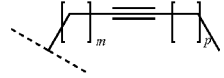
D2

D3 in which m=1 to 12 p=0 to 11 q=6 to 14 with m+p$\leq$12 and m+p$\geq$4; and most preferably a linear hydrocarbon-based chain containing 11 carbon atoms, which is saturated, or unsaturated between carbon atoms 4 and 5;

E and G represent NHC(O)CH$_3$;

$R^1$ represents H or C(O)CH$_3$;

$R^2$, $R^3$, $R^5$, $R^6$ and $R^7$ represent a hydrogen atom;

$R^4$ represents a substituent chosen from H, C(O)CH$_3$ and C(O)NH$_2$;

$R^8$ represents a substituent chosen from H, fucosyl, methylfucosyl, sulfofucosyl, acetylfucosyl, arabinosyl, SO$_3$H, SO$_3$Li, SO$_3$Na, SO$_3$K and SO$_3$N(C$_{1-8}$alkyl)$_4$;

$R^9$ represents a hydrogen atom;

in particular, the compounds for which $R^8$ represents H, $SO_3H$, $SO_3Li$, $SO_3Na$, $SO_3K$, $SO_3N(C_{1-8}alkyl)_4$ or a substituent of formula:

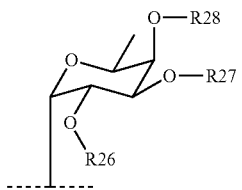

in which $R^{26}$ represents a substituent chosen from H and $CH_3$, preferably H;

$R^{27}$ and $R^{28}$ represent, independently of each other, a substituent chosen from H, $C(O)CH_3$, $SO_3H$, $SO_3Li$, $SO_3Na$, $SO_3K$ and $SO_3N(C_{1-8}alkyl)_4$, preferably $R^{27}$ and $R^{28}$ represent H.

As examples of compounds according to the invention that are particularly advantageous and preferred, mention may be made of the compounds corresponding to one of the following formulae:

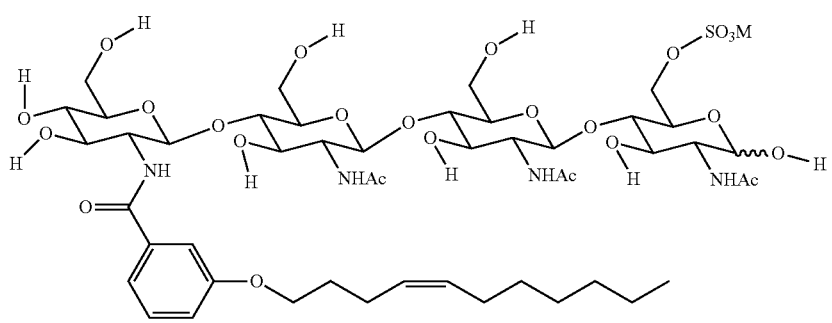

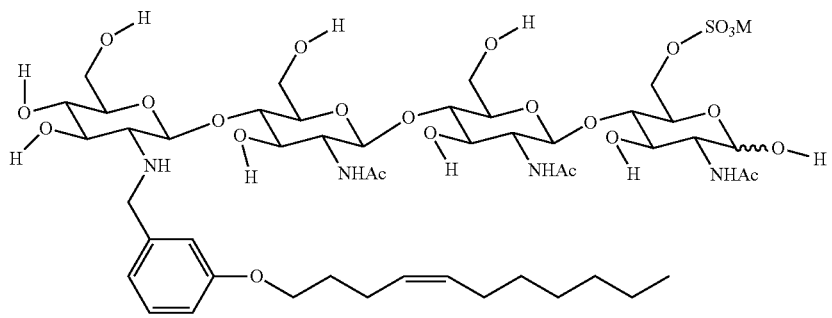

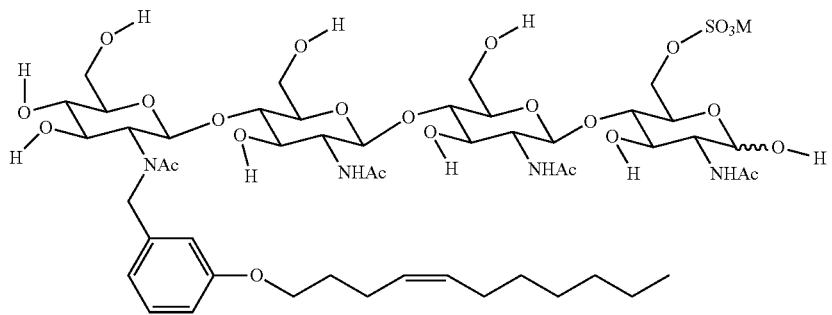

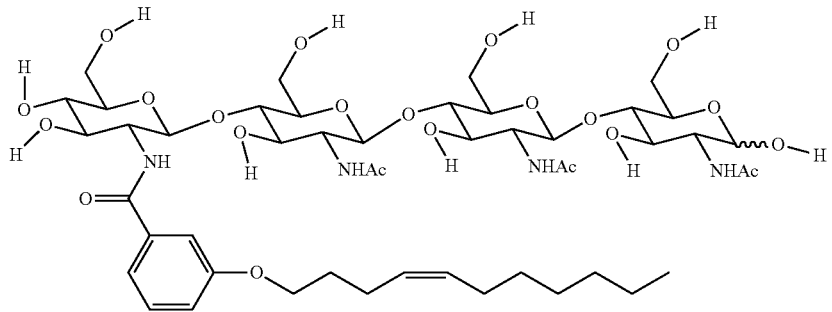

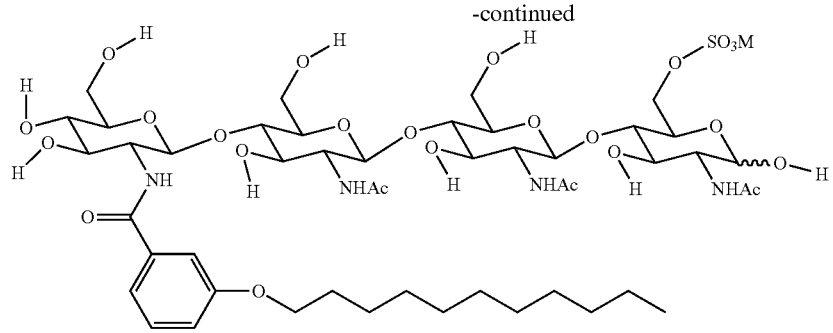
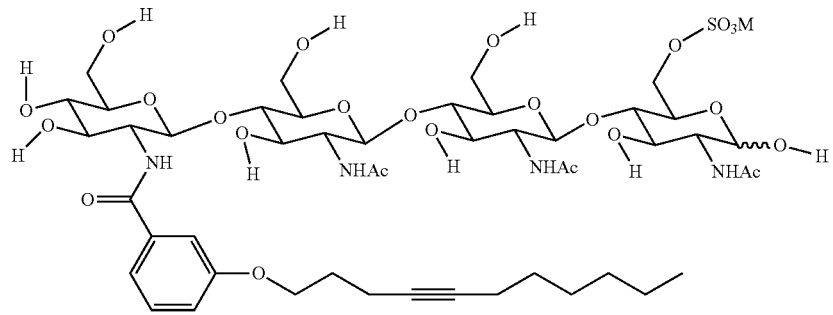
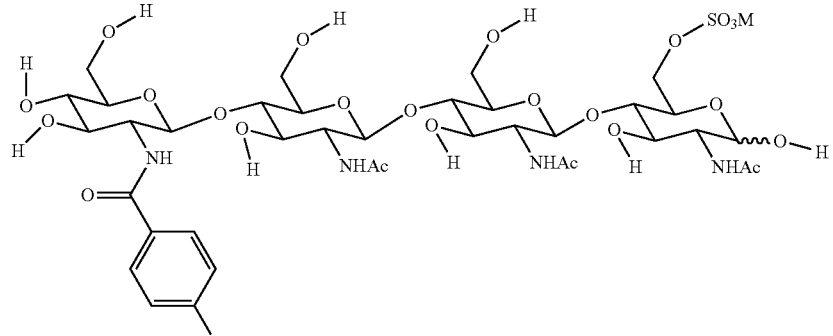
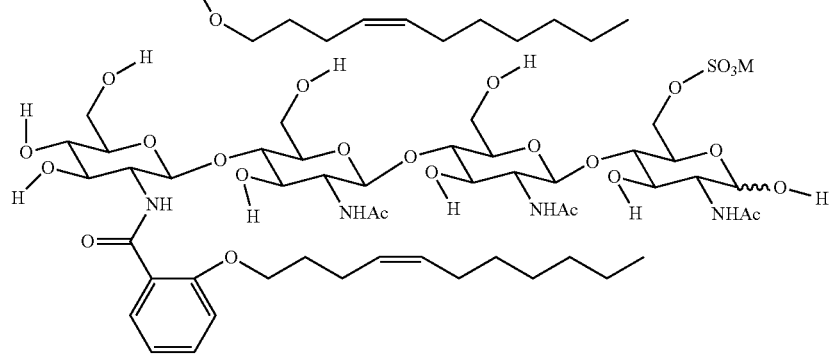
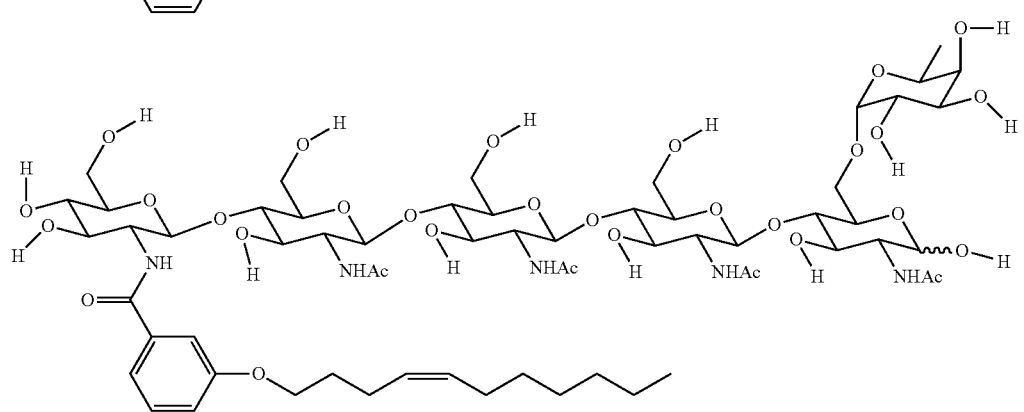

in which, when it is present, M represents a cation chosen from $H^+$, $Li^+$, $Na^+$, $K^+$ and $(C_{1-8}alkyl)_4N^+$.

Besides the compounds of the invention that have just been specifically described, the variants of combinations of possible substituents for the formulae (I), (Ia), (Ib), (Ic), (Id) and (Ie) especially, also form part of the invention.

It is known that a chitin oligomer not containing a lipid chain is not active, and that the degradation of the Nod factors by breaking the amide bond in the rhizosphere thus leads to a loss of activity. In order to limit, or even prevent, this degradation, a series of analogous compounds, some of which are more stable than the natural Nod factors, was prepared.

II-1. Structure of Compounds According to the Invention

Compounds containing a meta-substituted benzamide group were prepared. It is preferred to keep identical the total number of atoms along the chain (16) and also the unsaturation of cis type in position 9. In practice, for the production of the starting materials, the lipid chain may be linked to the aromatic ring via an oxygen atom.

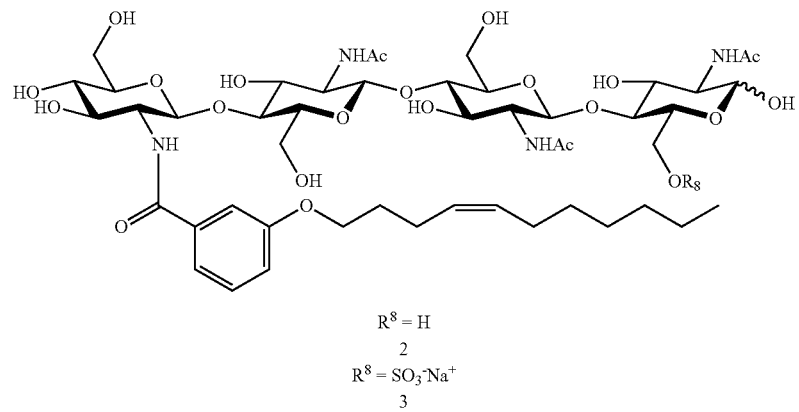

$R^8 = H$
2
$R^8 = SO_3^-Na^+$
3

An analog 4 containing a meta-substituted benzylamine function, and also an N-acetylated analog 5, which makes it possible to regain the overall charge of the natural product, were also synthesized. These analogs were prepared in the sulfated series.

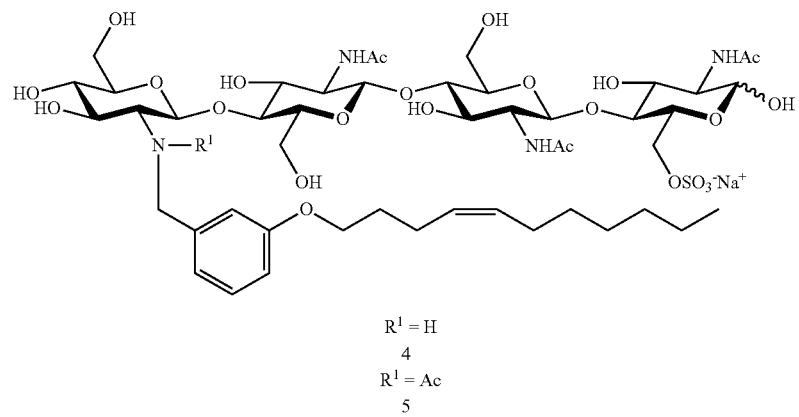

$R^1 = H$
4
$R^1 = Ac$
5

Two other sulfated analogs, one containing a fully saturated chain and the other an unsaturated chain of alkyne type, make it possible to study the effect of the unsaturation of Z type in position 9 present on the natural product.

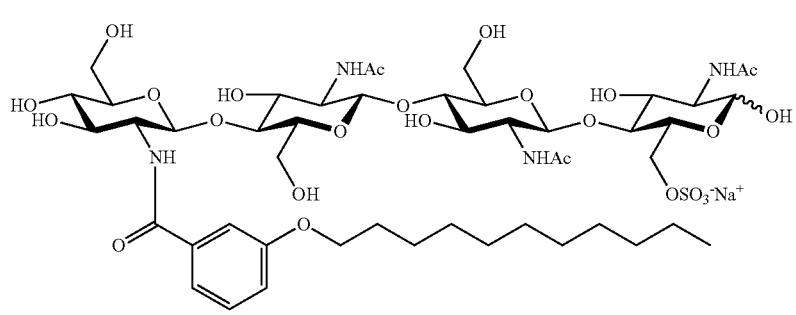

6

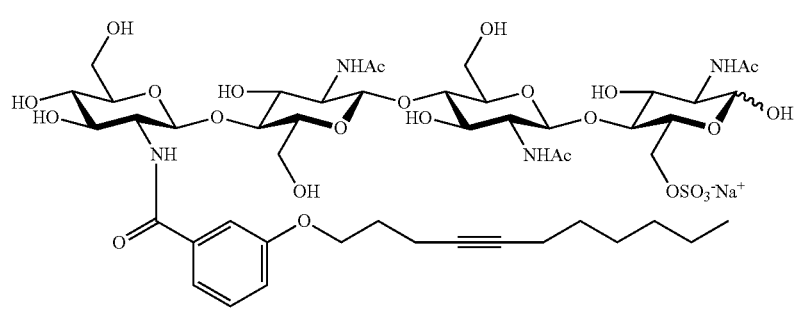

7

Finally, two sulfated analogs, the substitution on the aromatic ring of which is in the ortho position for one and in the para position for the other, make it possible to study the effect of the unsaturation of trans type located in position 2 on the natural product.

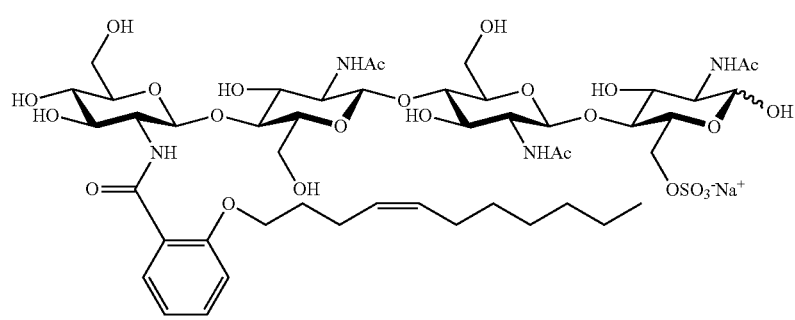

8

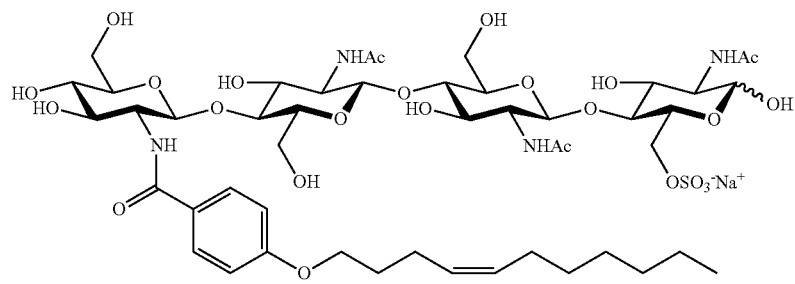

9

Finally, an analog, derived from a fucosyl pentamer, bearing a meta substitution on the chain, was prepared.

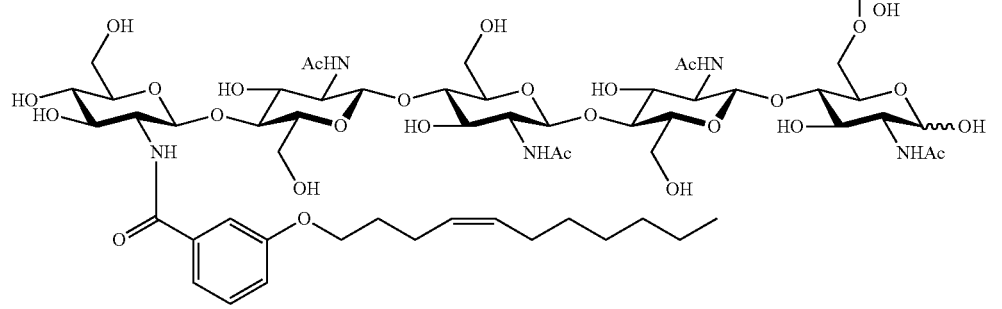

10

The references for the biological tests are the following compounds:

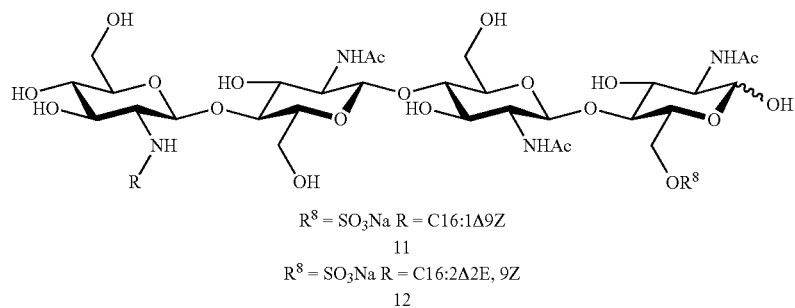

$R^8 = SO_3Na$  $R = C16:1\Delta9Z$
11

$R^8 = SO_3Na$  $R = C16:2\Delta2E, 9Z$
12

II-2. Synthesis of the Various Aromatic Chains

For the benzamide LCOs, the coupling with the amino tetramer is performed with a benzoyl chloride (acylation) and for the benzyl LCOs, with a benzaldehyde (reductive alkylation).

II-2.1. Synthesis of Aromatic Chains Meta-Substituted with the undec-4Z-enyloxy Chain According to the reaction scheme below, the methyl ester 15 is prepared, from which reduction to the aldehyde or saponification to the acid (acyl chloride precursor) may be envisaged.

To do this, 1-iodoundec-4Z-ene 13 is used to alkylate methyl 3-hydroxybenzoate. The ester 15 is isolated in a yield of 76%.

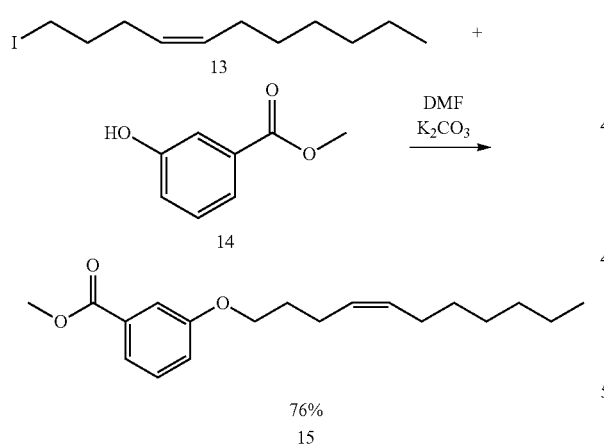

Conversion of the ester to the aldehyde 17 is performed in two steps.

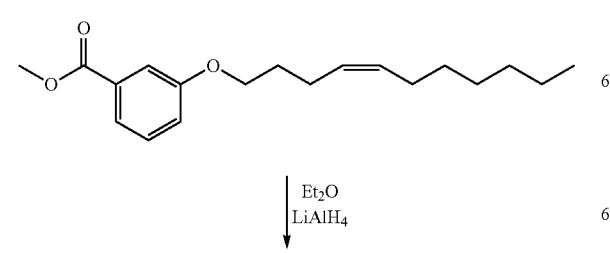

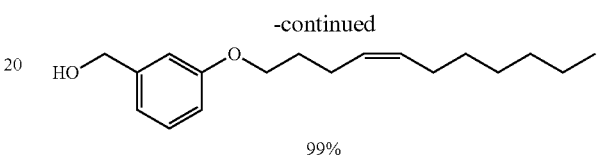

99%
16

CH$_2$Cl$_2$
PCC

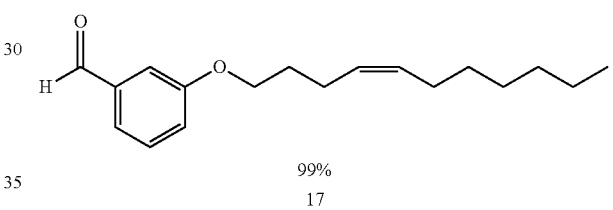

99%
17

Moreover, the acyl chloride 19 is obtained by saponification of the ester 15 followed by reaction with oxalyl chloride.

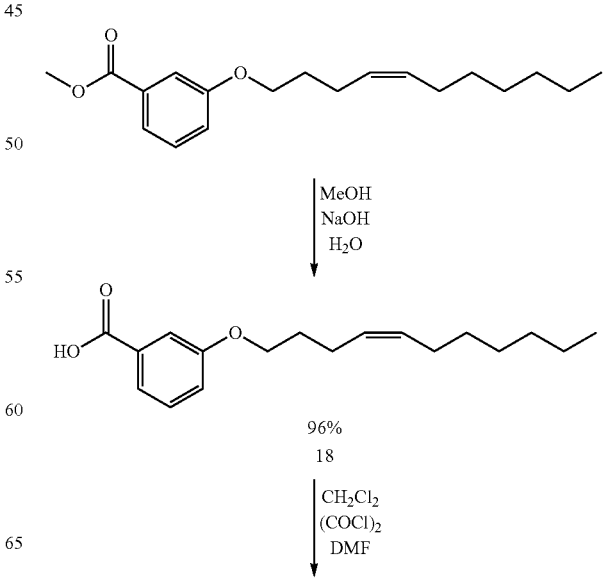

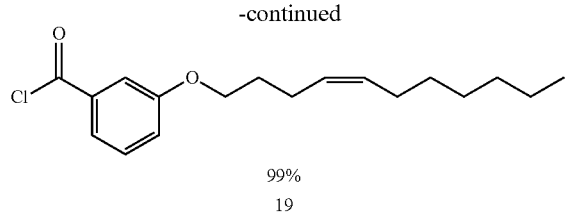
II-2.2. Synthesis of Aromatic Chains Meta-Substituted with undecanyloxy and undec-4-ynyloxy Chains
The same procedure with 1-bromoundecane or 1-iodoundec-4-yne in anhydrous DMF, followed by saponification and formation of the chloride, lead to the acid chlorides 23 and 27.
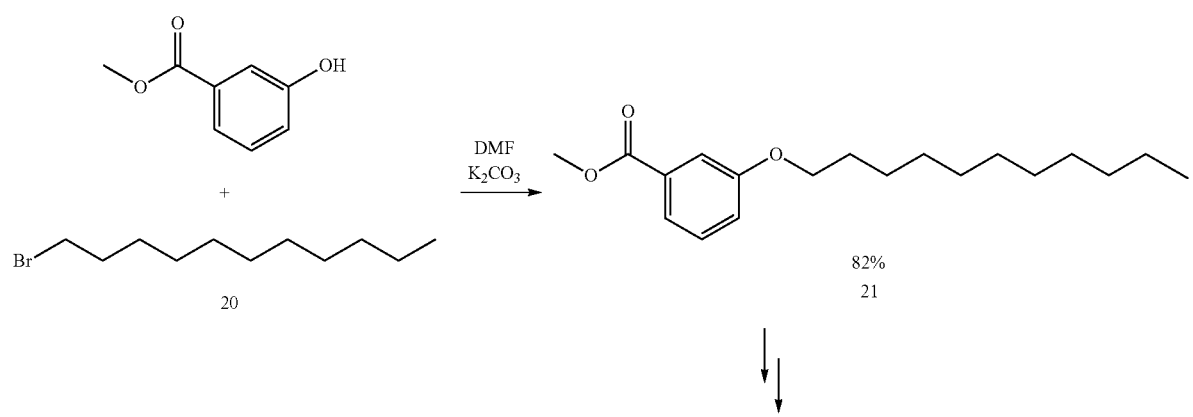
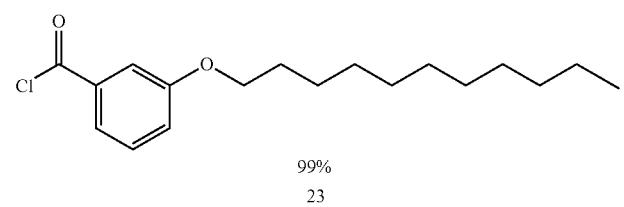
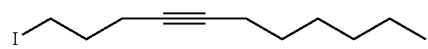
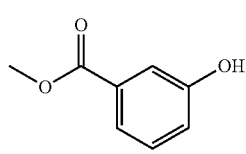
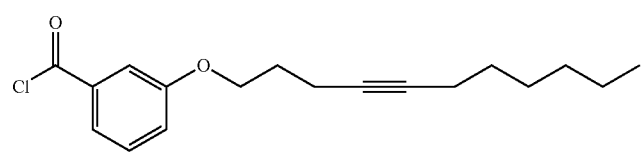

II-2.3. Synthesis of Aromatic Chains Ortho- or Para-Substituted with the undec-4Z-enyloxy Chain
The acid chlorides 31 and 35 are similarly prepared from 29 and 33, which are obtained as previously by Williamson coupling of 1-iodoundec-4Z-ene 13 with methyl 2-hydroxybenzoate 28 (or methyl salicylate) in a yield of 66%, and with methyl 4-hydroxybenzoate 32 in a yield of 79%.
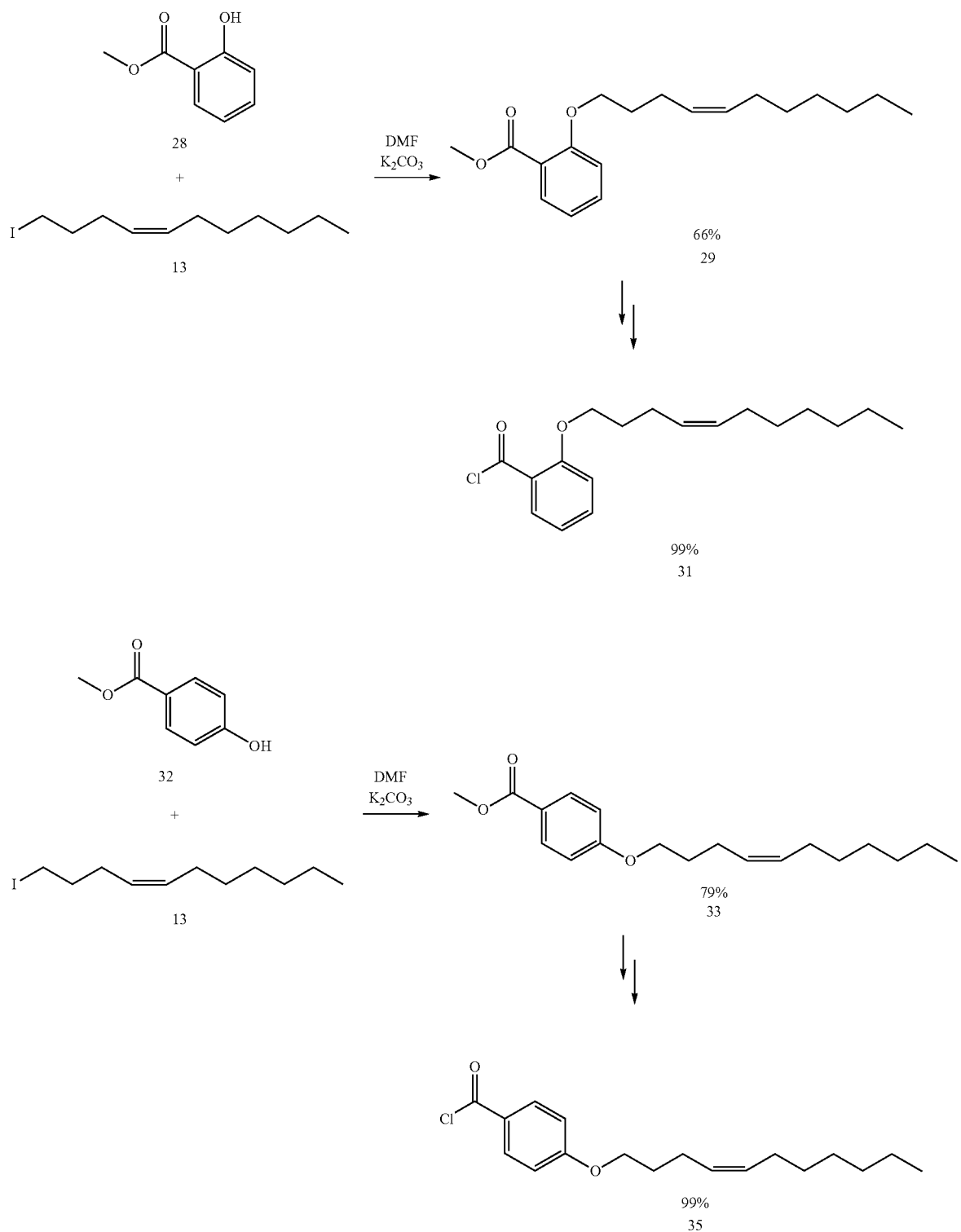

The saponifications and conversions to chloride are quantitative in both cases.

II-3. N-acylation of the Sulfated Tetramer CO—IV(NH₂, S) with the Various Benzoyl Chlorides

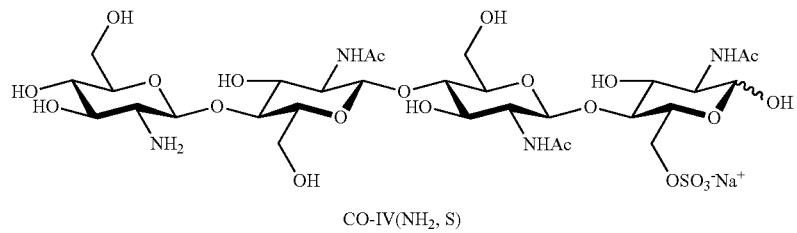

CO-IV(NH₂, S)

II-3.1. Coupling with 3-(undec-4Z-enyloxy)benzoyl chloride 19

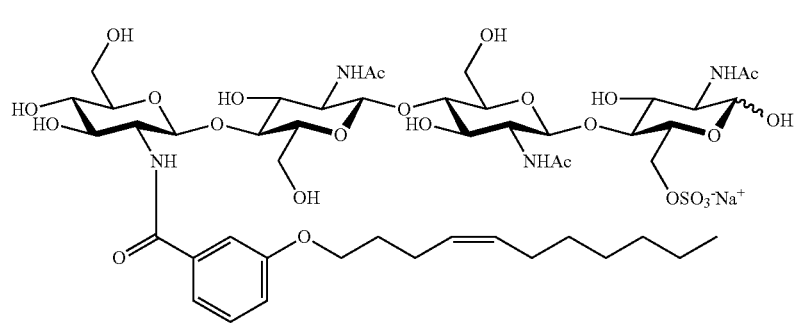

3

The coupling may be performed by dissolving the starting material in a DMF-water mixture in the presence of sodium hydrogen carbonate. Under these conditions, only the free amine is acylated. With 6 equivalents of chloride and after reaction for 18 hours, a conversion of about 60% is achieved, but the reaction is highly selective. 33% of desired product 3 are thus isolated. The purity of the product is checked by HPLC.

The ultraviolet (UV) absorption spectrum of product 3 is substantially different from that of the reference compound 12, especially due to the presence in 3 of an absorption peak at 289 nm. Such a peak, due to the benzamide group, does not exist for compound 12. This perfectly illustrates the UV properties of some of the compounds according to the invention making them easy to assay, in contrast with the natural Nod factors.

In contrast with compound 12, compound 3 also has a characteristic fluorescence at 345 nm when it is excited at 289 nm.

II-3.2. Coupling with 3-(undecanyloxy)benzoyl chloride 23 and 3-(undec-4-ynyloxy)benzoyl chloride 27

The same procedure as for the preceding derivative is repeated, i.e. dissolution in a DMF-water mixture and use of several equivalents of chloride.

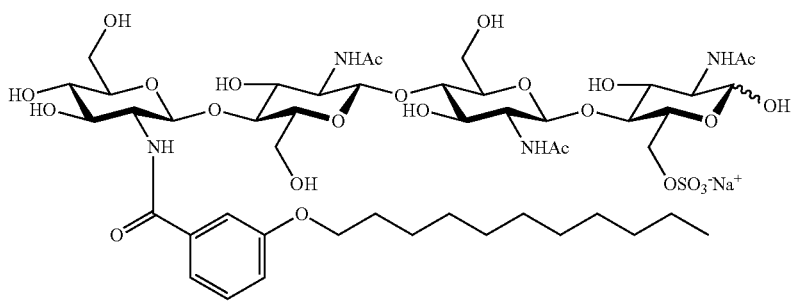

6

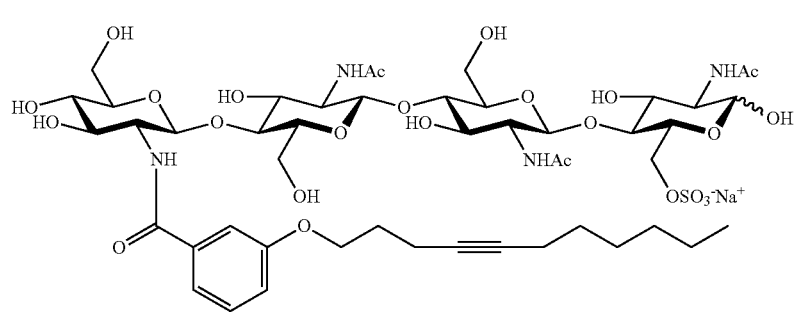

7

20

Under these conditions, the saturated analog 6 is obtained in a yield of 32% (and 47% conversion) and the analog containing a triple bond 7 in a yield of 31% (and 70% conversion). The purity is also checked by HPLC.

II-3.3. Coupling with 2-(undec-4Z-enyloxy)benzoyl chloride 31 and 4-(undec-4Z-enyloxy)benzoyl chloride 35

For these two analogs, by adopting a similar protocol, a yield of 48% is obtained for the ortho-substituted derivative 8 and a yield of 40% is obtained for the para-substituted derivative 9. For the two reactions, 4 equivalents of chloride were used. The purity is also checked by HPLC.

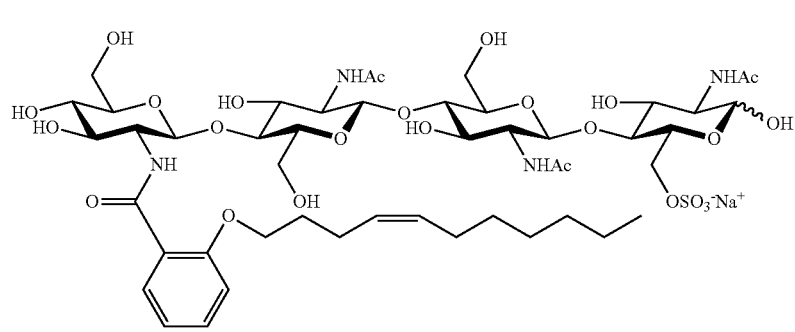

8

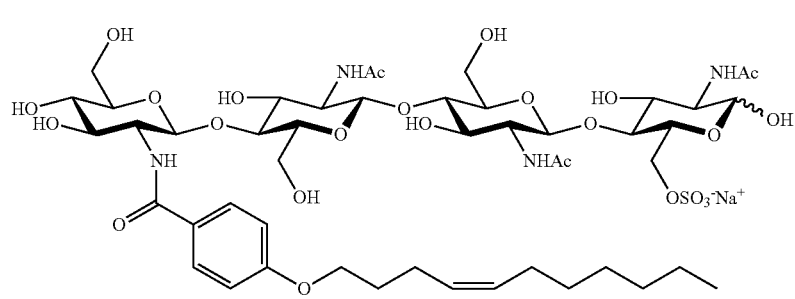

9

II-4. N-Acylation of the Nonsulfated Tetramer CO—IV(NH₂) with 3-(undec-4Z-enyloxy)benzoyl chloride 19

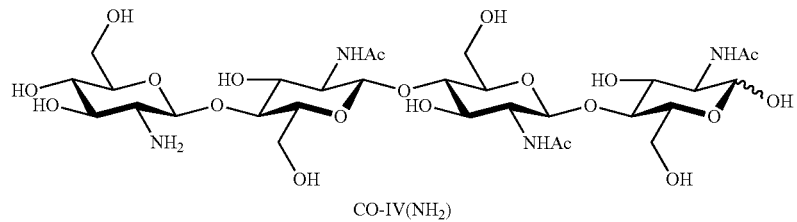

CO-IV(NH₂)

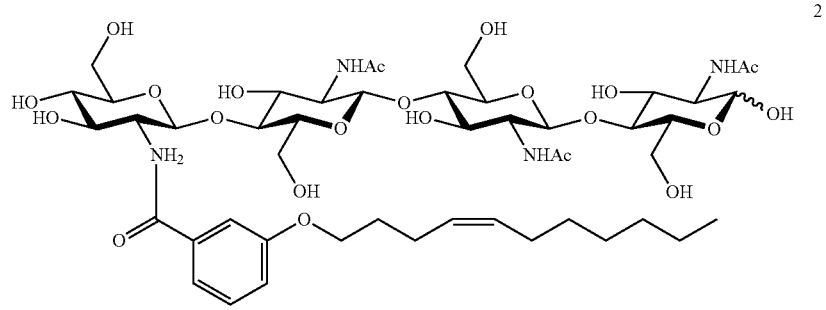

2

The reaction was carried out as previously in a DMF-water mixture, in which the starting material and the chloride are soluble. In order to facilitate the final purification, the reaction is performed in the presence of a basic Dowex resin (HCO₃⁻).

At the end of the reaction, the reaction medium is diluted with an acetonitrile/water mixture, and the expected compound is purified by filtration of the resin, passing through acidic Dowex (H⁺), resin, concentration and washing of the solid residue with ethyl acetate and then with water. 22% of the expected product 2 are thus isolated.

II-5. N-acylation of the Fucosylated Pentamer CO—V(NH₂, Fuc) with 3-(undec-4Z-enyloxy)benzoyl chloride 19

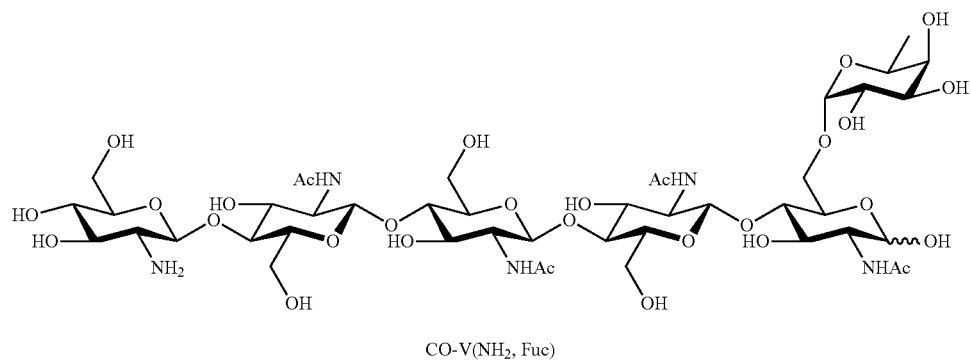

CO-V(NH₂, Fuc)

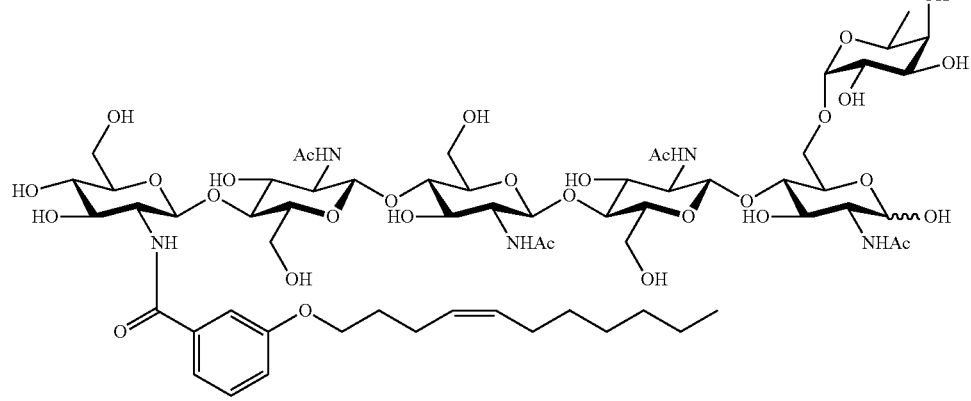

10

The reaction was performed as for the preceding product, in a DMF-water mixture, in which the starting material and the chloride are soluble. In order to facilitate final purification, the reaction is performed in the presence of a basic Dowex resin (HCO$_3^-$).

At the end of the reaction, the reaction medium is diluted with an acetonitrile/water mixture, and the expected compound is purified by filtration of the resin, passage through acidic Dowex resin (H$^+$), concentration and washing of the solid residue with ethyl acetate and then with water. 28% of the expected product 10 are thus isolated.

II-6. Reductive Alkylation of the Sulfated Tetramer with 3-(undec-4Z-enyloxy)benzaldehyde II-6.1. Alkylation of the Tetramer CO—IV(NH$_2$, S)

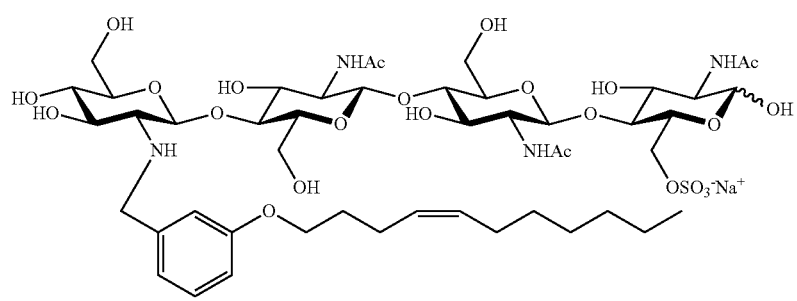

4

The reductive alkylation reaction was performed in anhydrous DMF in the presence of lithium bromide. With 12 equivalents of aldehyde and 15 equivalents of sodium cyanoborohydride, 71% of expected coupling product 4 are isolated by chromatography on silica gel after 24 hours.

II-6.2. N-Acetylation of the Coupling Product Obtained from the Reductive Alkylation

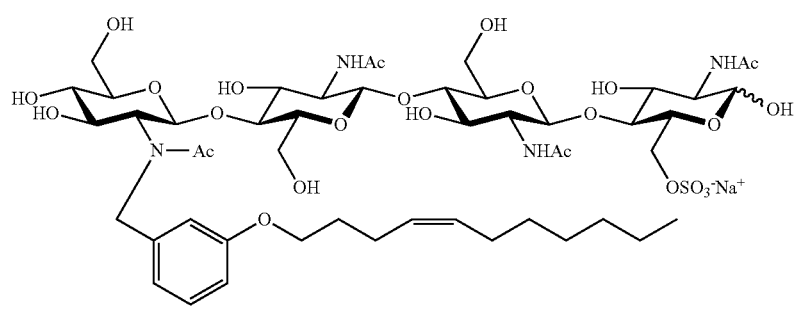

5

The reaction is performed in an ethyl acetate-methanol-water mixture by addition of acetic anhydride, in the presence of sodium hydrogen carbonate. After 12 hours, the starting material 4 is removed by passage through H$^+$ resin. After purification on silica, the expected product 5 is isolated in a yield of 77%. The purity is checked by HPLC.

II-7. Activity Tests

II-7.1 Activity Tests on Temperate Legumes of the Galegoid Group

Temperate legumes of the Galegoid group are nodulated by *rhizobia* that produce Nod factors with the hydrophobic chain having a double bond conjugated to the carbonyl group. This group includes important legume crops such as alfalfa, pea, broad bean, chickpea and clover.

The sulfated products are tested on alfalfa for induction of the formation of root nodules, and on the model legume *Medicago truncatula* for induction of the expression of a symbiotic gene coding for an early nodulin.

II-7.1. 1 Nodulation Tests on Alfalfa

Alfalfa plantlets are grown under axenic conditions in test tubes on a nitrogen-poor agar medium (Demont-Caulet et al., Plant Physiol., 120, 83-92, 1999). Untreated plantlets serve as control. Natural Nod or synthetic LCO factors are added at the concentrations indicated.

II-7.1.1.1 Results of Nodulation Tests

The benzamide derivative 3 meta-substituted with the undec-4Z-enyloxy chain shows advantageous activity, the activity being similar to that of the sulfated tetramer 11 acylated with the reference C16:1Δ9Z chain as shown in FIG. 1.

Figure 2:
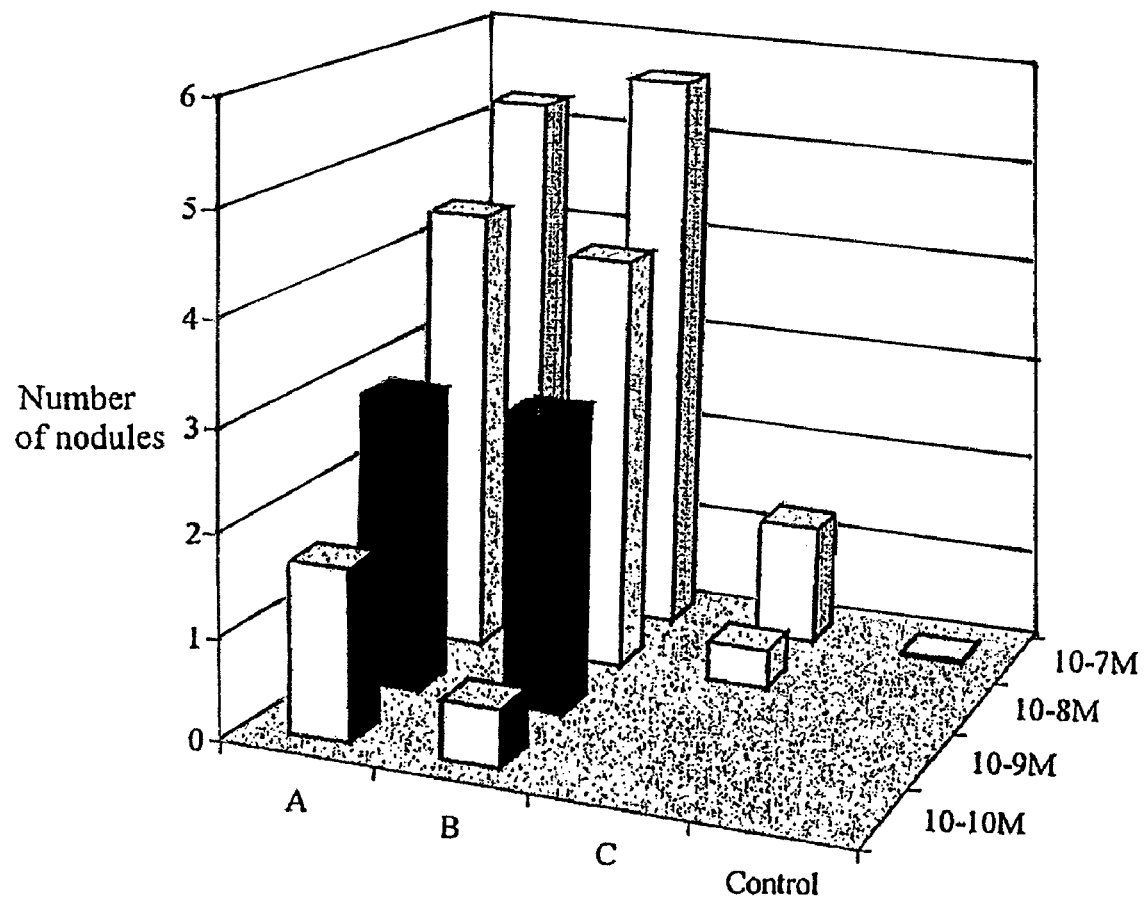
FIG. 2 illustrates the relative activities of the benzyl derivative 4 to the benzamide derivative 3.

The benzyl derivative 4 has moderate activity relative to the benzamide derivative 3 as shown in FIG. 2.

Figure 3:
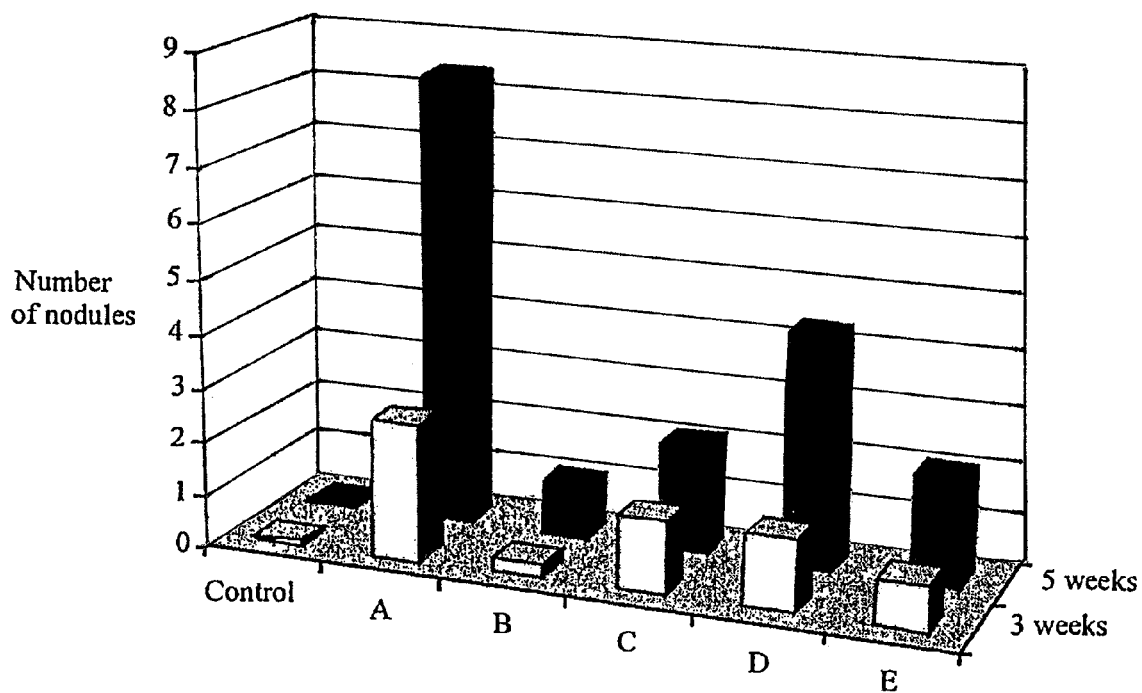
FIG. 3 illustrates the relative response and activity of the N-acetylation of the benzyl derivative 4 with the benzamide derivative 3.

Finally, the N-acetylation of the benzyl derivative 4 leads to an improvement in the response, but the activity remains lower than that of the benzamide derivative 3 as shown in FIG. 3.

These results indicate the importance of the amide bond. The results obtained with these benzamide derivatives confirm the effect of the amide-double bond conjugation present on the natural compound.

Figure 4:
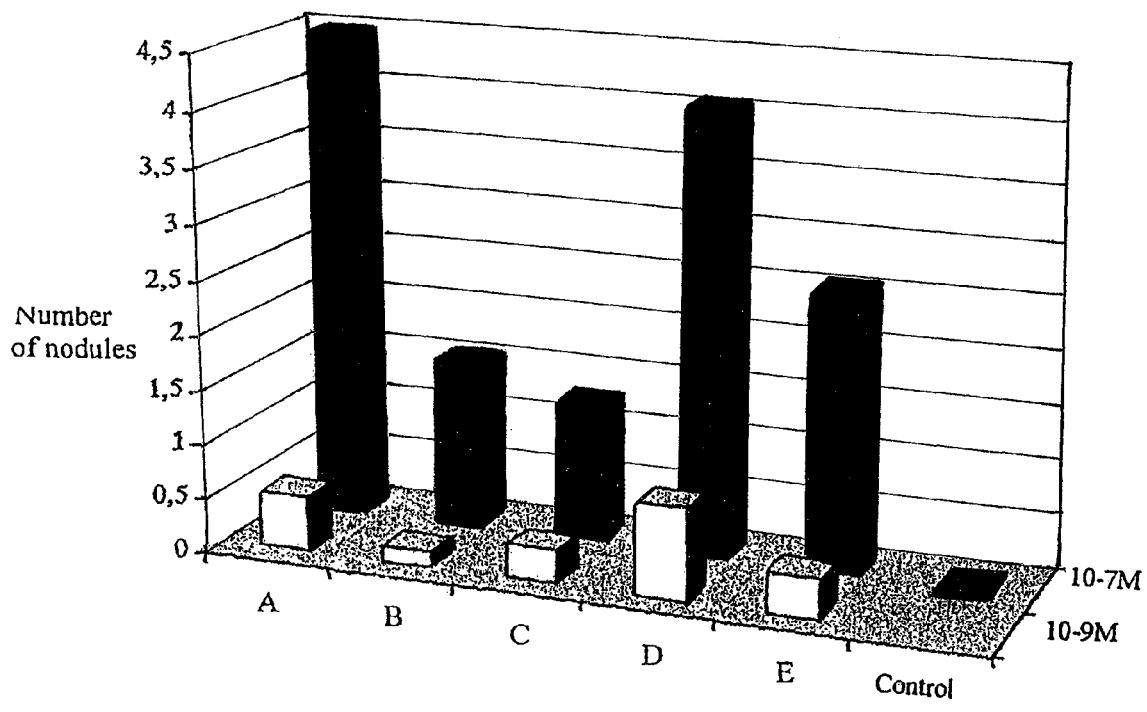
FIG. 4 illustrates the activity with an unsaturation in position 4.

The benzamide 7 meta-substituted with the undec-4-ynyloxy chain shows activity comparable to that of the benzamide derivative 3, whereas the benzamide compound 6 substituted with the fully saturated chain shows slightly lower activity. These results indicate that an unsaturation in position 4 may lead to an increase in activity as shown in FIG. 4.

The tests relating to the benzamide derivatives 8 and 9 ortho- and para-substituted with the undec-4Z-enyloxy chain reveal analogs that are less active than the meta-substituted benzamide derivative 3. The meta substitution is thus preferred as mimic for an unsaturation of trans type.

II-7.1.2. Tests of Induction of Early Nodulin on *Medicago truncatula*

These tests are performed to determine whether the synthetic LCOs induce symbiotic responses by activation of the same signal transduction pathway as the natural Nod factors. The tests are performed on the model legume *Medicago truncatula*. The activity of the sulfated benzamide derivative 3, meta-substituted with the undec-4Z-enyloxy chain, which is the most active synthetic compound in the nodulation test on alfalfa, is studied on "wild-type" plants and on a mutant in the gene DMI1 which is altered in the transduction of the Nod factor signal (Catoira et al. *Plant Cell*, 12, 1647-1665, 2000). The compound that serves as reference is the sulfated tetramer 12 acylated with the C16:2Δ2E,9Z chain, which is an analog of the natural Nod factor. The control is the plant cultivated in the absence of LCO.

II-7.1.2.1 Reporter Gene

It is generally difficult to determine the regulation of expression of a particular gene, during a biological process, since most of the specific products of these genes are not readily detectable or measurable. To overcome this problem, a technique of fusion with "reporter genes" is used, i.e. genes coding for a readily assayable protein. The fusion consists in combining the DNA sequence containing the gene regulatory regions that it is desired to study, with the DNA sequence of the reporter gene. The assembly is then reintroduced into the plant by transformation. Thus, if the target gene is expressed, the reporter gene is automatically expressed. It is then a matter of assaying the reporter gene protein.

In order to avoid a negative interaction with the activity of the plant, reporter genes that do not code for any enzyme normally formed by the plants are used. One of the enzymes most commonly used is β-glucuronidase (GUS) from *Escherichia coli*, a hydrolase that catalyzes the cleavage of a large is variety of β-glucuronides. As commercial substrate of this enzyme, it is possible to use: X-Gluc (Sigma B-4782): 5-bromo-4-chloro-3-indolyl glucuronide; the anion formed has a blue color.

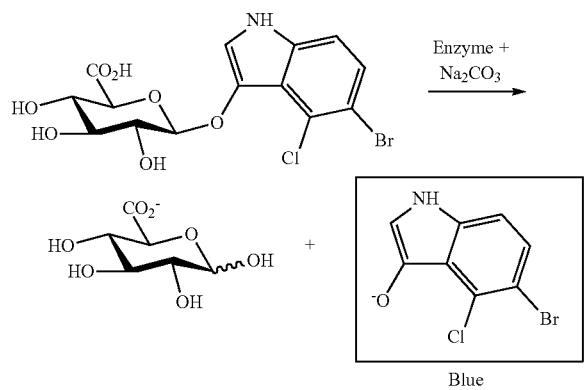

II-7.1.2.2 Enod11::GUSA

The genes for the legumes involved in modulation may be classified into two major types:

early nodulin genes (ENOD), which are activated in the first days of the infection and activation of the nodulation process;

late nodulin genes, which are not activated until several days after the application of the bacteria, and do not intervene until the period of maturation of the nodules.

A new gene of *Medicago truncatula*, MtENOD11, coding for an RPRP (Repetitive proline-rich protein), and transcribed during the first steps of infection of nodulation on the nodule roots and tissues was identified (Journet et al. *Mol. Plant-Microbe Interact.*, 14, 737-748, 2001). Using the transgenic *Medicago truncatula* plant expressing the fusion MtENOD11::GUSA, it is possible to determine whether a Nod factor analog added to the culture medium of the plant has induced transcription of the ENOD11 gene.

For the ENOD11 transcription tests, a Fahraeus medium is used as for the modulation tests, but without agar. The seedlings are placed on paper in pockets containing the culture medium. The responses of two types of transgenic plants bearing the MtENOD11::GUS: fusion are compared: a "wild-type" (WT) Jemalong plant and a plant bearing a mutation in the DMI1 gene, which is incapable of transducing the Nod factor signal. The plants are left to grow for 5 days and the plantlets are then treated with various concentrations of LCO. After 6 hours, the plantlets are removed and placed in aqueous medium containing X-Gluc for 1 to 2 hours. The number of roots giving a characteristic blue response is then counted.

Figure 5:
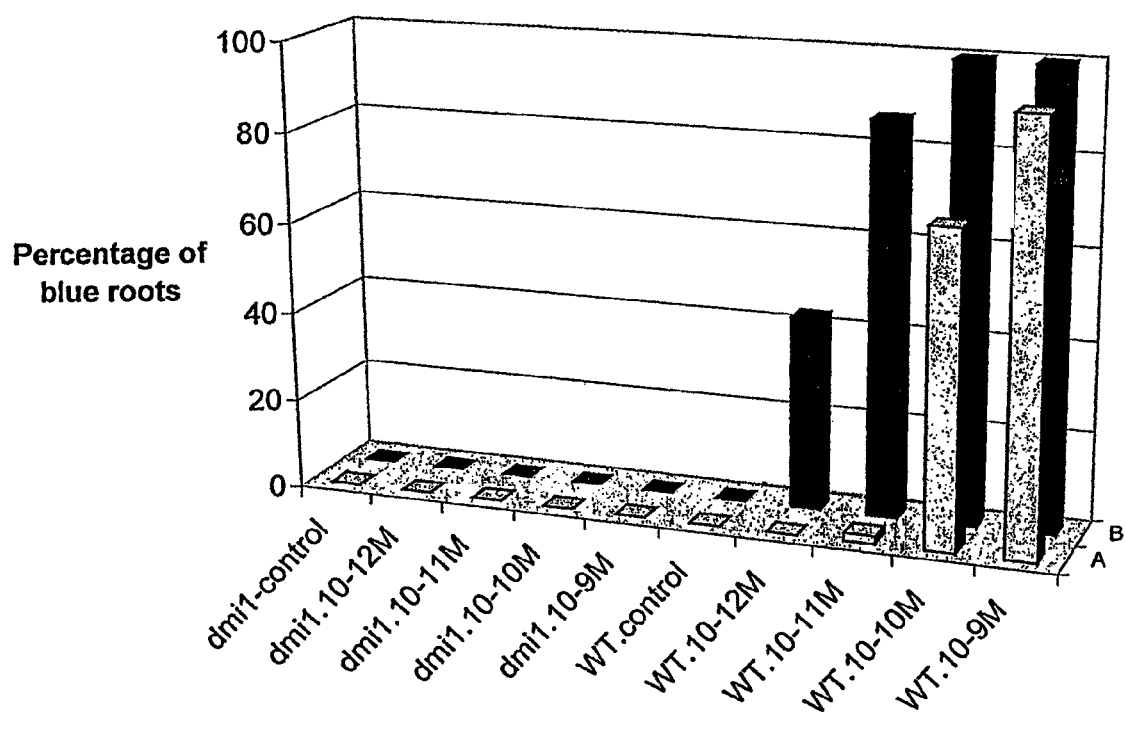
FIG. 5 illustrates test sensitivity.

This test is relatively sensitive, to the extent that it is possible to work at LCO concentrations that are lower than those for the nodulation tests as shown in FIG. 5.

It is found that the benzamide derivative 3 is approximately 10 times less active than the reference compound, the acylated tetramer 12. Moreover, as for the reference compound 12, the benzamide derivative 3 does not induce any response in the plants bearing the DMI1 mutation. It may thus be concluded that the synthetic compound of benzamide type activates the transcription of the ENOD11 gene via the same transduction pathway as that activated by the natural Nod factors.

II-7.2 Activity Tests on Other Legumes

Sulfated benzamide derivatives have been shown to have similar biological activity on the roots of *Medicago* species than the major natural sulfated *Sinorhizobium meliloti* Nod factor which is N-acylated with a C16:2 chain. It has been hypothesized that the benzamide derivative is a good structural mimic of the natural *S. meliloti* Nod factors having an amide bond between the chitin oligomer backbone and the hydrophobic chain with a double bond conjugated to the carbonyl group. This type of alpha-beta conjugated double bond is characteristic of Nod factors from *rhizobia* that nodulate temperate legumes such as alfalfa, clover, pea, broad bean, chickpea, etc. . . . In contrast, *rhizobium* that nodulate legumes of tropical origin such as soybean, peanut, bean, cowpea, etc. . . . produce Nod factors in which the carbonyl group is not conjugated to a double bond. It was thus important to determine whether a benzamide analog of a natural Nod factor with no conjugated double bond would also exhibit biological activity on the cognate legume.

This question was addressed by using the *Lotus corniculatus* root hair deformation bioassay. *Lotus corniculatus* is a forage crop which is nodulated by *rhizobia* which produce Nod factors quite similar to those produced by *rhizobia* which nodulate soybean: the chitin oligomer backbone has five glucosamine residues, the N-acyl chain is essentially vaccenic acid (C18:1) and the reducing glucosamine residue is not sulfated and is O-substituted by a fucosyl residue. *Lotus corniculatus* was chosen as a model system because seeds and seedlings are small sized and convenient to handle.

II-7.2.1 Root Hair Deformation Assay on *Lotus corniculatus*

Seeds of *Lotus corniculatus* (cv Rodeo) were sterilized. Germinated seeds with rootlets about 1 cm long were aseptically transferred onto Farhaeus soft agar plates. Plates were sealed with Parafilm and placed vertically for two days in a plant growth chamber (at 25° C., with a 16-hr light period, a relative humidity of 75%, OsramVFluora L 77 as the type of light, and light intensity at the level of the top of the plates of 30 µE·m-2·s-1) to allow plant growth and root hair development. Then 2 ml of a Nod factor derivative sterile solution was poured to cover the *Lotus* root system, and after 30 nm, excess liquid was removed. A further incubation was performed for 16 hr in the plant growth chamber. The roots of the five plants were transferred between slide and cover slip and observed by bright field microscopy after staining by methylene blue.

Hair deformation (Had) activity was estimated by a limit dilution method. Nod factor derivatives were applied at concentrations ranging from 10-7 M to 10-11 M. The activity of two DP5 chitin derivatives were compared, the soybean Nod factor and its benzoylated analog 10. Both compounds were O-fucosylated at the reducing end, but differed by the N-substitution on the terminal non-reducing glucosamine residue, either C18:1 N-acylated like the soybean Nod factor or N-benzoylated. Each compound was dissolved in water/ethanol 50/50; 0.01% Chaps was added at a concentration of 1 mM. These stock solutions were then diluted in water.

To estimate the plant response, a criterion of clear-cut hair branching was chosen (numerous branching at more than one site on the root system), and plants exhibiting these pronounced reactions were classified as <<+>>. The statistical significance (at the P=0.05) of the proportion of <<+>> responses was calculated using the ratio comparisons based on the Fisher's <<Exact>> test (SAS software). Experiments were carried out twice. Data are given in the following Table:

TABLE

| | Root hair deformation assay on *Lotus corniculatus* | | | | |
|---|---|---|---|---|---|
| | $10^{-7}$ M | $10^{-8}$ M | $10^{-9}$ M | $10^{-10}$ M | $10^{-11}$ M |
| Acylated compound | + | + | + | + | − |
| Benzoylated compound 10 | + | + | + | − | − |

Fifteen plants were used for each treatment and each dilution. Sixty six untreated control plants were used to estimate the intrinsic plant variability for the Hair deformation character. The responses were classified "+" when the proportion of Had+ was significantly higher (at the probability level P=0.05) among the treated plants compared with the untreated control. Data were analysed using the Fisher's "Exact" test.

These experiments show that the benzamide derivative 10 has a high activity on the *Lotus corniculatus* root hair bioassay, with a significant activity at nanomolar concentration. It may thus be concluded that benzamide derivatives could be used to stimulate symbiotic activity on legumes that are nodulated by *rhizobia* which produce Nod factors that have no alpha-beta conjugated double bonds on the acyl chain, such as soybean.

III Examples

For the aromatic derivatives, the ring is numbered according to the official nomenclature.

For the description of the NMR spectra for the CO and LCO, the sugars are numbered starting with the reducing end:

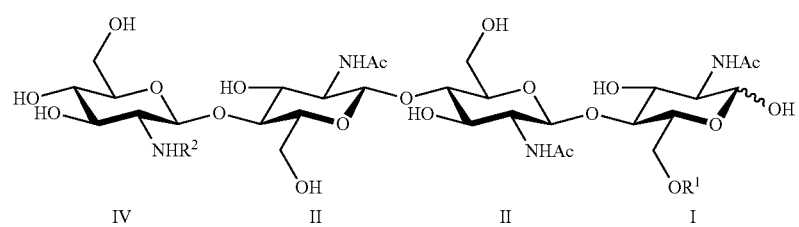

The conventional numbering is adopted on each sugar.

2-acetamido-4-O-{2-acetamido-4-O-[2-acetamido-2-deoxy-4-O-(2-deoxy-2-(N-3-(undec-4Z-enyloxy) benzoyl)amino-β-D-glucopyranosyl)-β-D-glucopyranosyl]-2-deoxy-β-D-glucopyranosyl}-2-deoxy-D-glucopyranose (2)

Mass Spectrum:
Positive electrospray (ESI) ionization m/z=1183.5 [M+Na]+

2-acetamido-4-O-{2-acetamido-4-O-[2-acetamido-2-deoxy-4-O-(2-deoxy-2-(N-3-(undec-4Z-enyloxy) benzoyl)amino-β-D-glucopyranosyl)-β-D-glucopyranosyl]-2-deoxy-β-D-glucopyranosyl}-2-deoxy-6-O-sulfo-D-glucopyranose, sodium salt (3)

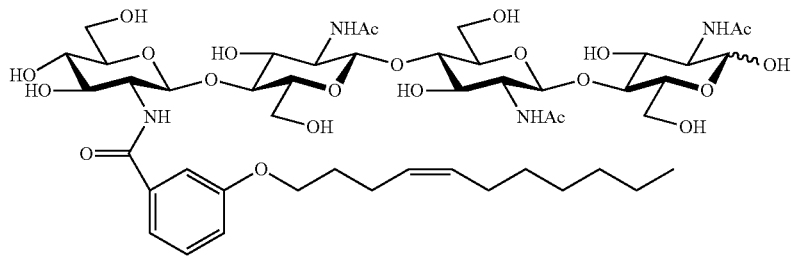

7.2 mg of CO—IV(NH$_2$) are dissolved in 200 μl of water and 500 μL of DMF, and are then heated to 40° C. 36 mg of Dowex 1×2-100 resin (HCO$_3^-$) are then added, followed by addition of 160 μL of a solution of 19 in distilled THF (26 μmol). 108 mg of HCO$_3^-$ resin and 480 μL of the solution of 19 in distilled THF (78 μmol) are added in three portions over 48 hours. The reaction medium is diluted with 3 mL of 1/1 acetonitrile/water mixture, the reaction medium is collected, leaving the resin, and is then filtered through cotton wool to remove the entrained resin beads. The filtrates are passed through a Dowex 50×8-100 resin (H$^+$) and then concentrated,

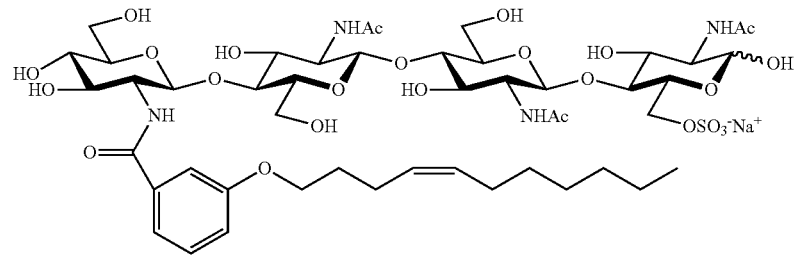

and washing of the solid residue is then performed with ethyl acetate, and then with water. 2 mg of a white powder are obtained, i.e. a yield of 22%.

$^1$H NMR (400 MHz, 20/1 DMSO-d6/D$_2$O) δ (ppm):
7.40-7.31 (m, 3H, ArH-2, ArH-6 and ArH-5), 7.04 (m, 1H, ArH-4), 5.41-5.35 (m, 2H, CH=CH), 4.87 (d, 0.7H, J$_{1,2}$=2.3 Hz, H-1α$^I$), 4.52 (d, 1H, J=8.3 Hz, H-1β$^{IV}$), 4.42 (d, 0.3H, J=8.0 Hz, H$_1$-β$^I$), 4.33 (2d, 2H, J=8.3 Hz, H-1β$^{II-III}$), 3.98 (t, 2H, J=6.0 Hz, ArOCH$_2$—CH$_2$) 3.78-3.05 (m, 24H, other sugar Hs), 2.16 (dt, 2H, J=5.8 and J=6.7 Hz, CH$_2$—CH=CH), 1.97 (dt, 2H, J=6.0 and J=6.2 Hz, CH=CH—CH$_2$), 1.81/1.81/1.79 (3s, 9H, 3 COCH$_3$), 1.80-1.72 (m, 2H, ArOCH$_2$—CH$_2$—CH$_2$), 1.28-1.13 (m, 8H, 4 CH$_2$), 0.81 (t, 3H, CH$_3$, J=6.5 Hz).

15 mg of CO—IV(NH$_2$,S) (17 μmol) are dissolved in 100 μL of water and 250 μL of DMF. 3 mg of sodium hydrogen carbonate (34 μmol) are then added, followed by addition of 20 μL of a solution of 19 in THF at a concentration of 0.25 g/mL (16.4 μmol). The reaction medium is heated to 60° C. and 100 μL of the solution of 48 and 10 mg of sodium hydrogen carbonate are added in six portions over 18 hours. After concentrating, the residue is purified by placing it in dichloromethane(DCM)/methanol (5/1) on a column of silica, while diluting it greatly, in order to remove the lipid chain. The elution is then performed with E/M/W (7/2/1 Ethyl acetate/Methanol/Water). 6.5 mg of a white solid are thus isolated, i.e. a yield of 33%.

$^1$H NMR (400 MHz, DMSO-CD$_3$OD (½)) δ (ppm):

7.48 and 7.41 (m, 2H, ArH-2 and ArH-6), 7.36 (dd, 1H, Ar H-5, $J_{5,6}$ 7.7 Hz and $J_{5,4}$ 8.1 Hz), 7.07 (ddd, 1H, ArH-4, $J_{4,2} \approx J_{4,6}$ 1.4 Hz), 5.41 (m, 2H, CH=CH), 5.03 (d, 0.8H, H-1$\alpha^I$, $J_{1*a*,2}$ 3.2 Hz), 4.68-4.59-4.50 (3 d, 3H, H-1$\beta^{II,III,IV}$, $J_{1\beta,2}$ 8.4 Hz, 8.5 Hz and 8.7 Hz), 4.56 (d, 0.2H, H-1$\beta^I$, $J_{1\beta,2}$ 7.7 Hz), 4.25-3.30 (m, 26H, CH$_2$—OAr, other Hs of the sugars), 2.25 (td, 2H, CH$_2$—CH=CH—CH$_2$, J 6.7 Hz and J 6.2 Hz), 2.10-1.90 (m, 11H, CH$_2$—CH=CH—CH$_2$ and 3 CH$_3$CO), 1.83 (tt, 2H, ArO—CH$_2$—CH$_2$—CH$_2$, J 6.7 Hz), 1.35-1.20 (m, 8H, 4 CH$_2$), 0.88 (m, 3H, CH$_3$)

Mass spectrum:
Negative ESI m/z=1139.4 [M−Na]−
UV: 289 nm
Fluorescence: $\lambda_{ex}$: 289 nm; $\lambda_{em}$: 345 nm 2-acetamido-4-O-{2-acetamido-4-O-[2-acetamido-2-deoxy-4-O-(2-deoxy-2-(N-3-(undec-4Z-enyloxy)benzyl)amino-β-D-glucopyranosyl)-β-D-glucopyranosyl]-2-deoxy-β-D-glucopyranosyl}-2-deoxy-6-O-sulfo-α-glucopyranose, sodium salt (4)

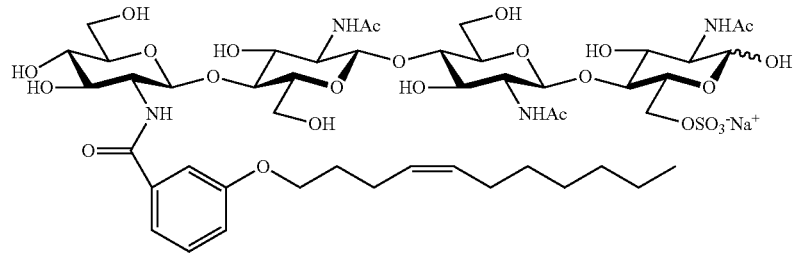

11 mg of CO—IV(NH$_2$,S) (12 µmol) are dissolved in 0.5 mL of DMF to which are added 12 mg of lithium bromide. 2 mg of sodium cyanoborohydride (32 µmol) and 100 µL of a solution of 17 in THF at a concentration of 73 mg/mL (26 µmol) are added. The reaction medium is heated at 40° C. for 4 hours. Every 2 hours, 2 equivalents of aldehyde and 2.5 equivalents of sodium cyanoborohydride are added, i.e. in total 12 equivalents of aldehyde and 15 equivalents of sodium cyanoborohydride. Although the conversion is not complete, the reaction is stopped by destroying the excess sodium cyanoborohydride with 0.5 N hydrochloric acid. When the evolution of gas has ended, the medium is diluted in water and freeze-dried. The resulting material is taken up in water, 5 mg of sodium hydrogen carbonate (59 µmol) are added to return to basic pH, and the resulting material is then coevaporated twice with methanol. The residual white solid is placed in DCM/methanol (5/1) on a column of silica, while diluting it greatly, in order to remove the lipid chain. The elution is then performed with E/M/W (5/2/1) and then (4/1/1). 10 mg of white needles are thus isolated, i.e. a yield of 71%.

$^1$H NMR (400 MHz, DMSO-CD$_3$OD (2/1)) δ (ppm):
7.31 (dd, 1H, ArH-5, $J_{4,5}$ 8.2 Hz and $J_{5,6}$ 7.8 Hz), 7.02 (m, 2H, ArH-2 and ArH-6), 6.90 (dd, 1H, ArH-4, $J_{4,6}$ 2.3 Hz), 5.51 (m, 2H, CH=CH), 5.08 (d, 0.8H, H-1$\alpha^I$, $J_{1\alpha,2}$ 3.1 Hz), 4.67 (m, 2.2H, H-1$\beta^{I,II,III}$), 4.47 (d, 1H, H-1$\beta^{IV}$, $J_{1\beta,2}$ 28.0 Hz), 4.06 (t, 2H, CH$_2$—OAr, J 6.3 Hz), 3.94 (s, 2H, NH—CH$_2$—Ar), 4.25-3.45 (m, 23H, other Hs of the sugars), 2.45 (dd, 1H, H$_2^{IV}$, $J_{1\beta,2} \approx J_{2,3}$ 8.8 Hz), 2.31-2.12 (2 m, 4H, CH$_2$—CH=CH—CH$_2$), 2.07-2.04-2.01 (3 s, 9H, 3 CH$_3$CO), 1.89 (tt, 2H, ArO—CH$_2$—CH$_2$—CH$_2$—CH=CH, J 6.9 Hz), 1.45-1.25 (m, 8H, 4 CH$_2$), 0.97 (t, 3H, CH$_3$, J 6.8 Hz)

$^{13}$C NMR (50 MHz, DMSO-CD$_3$OD (2/1)) δ (ppm):
172 (3 CH$_3$CO), 160 (ArC-3), 132-131-130 (ArC-1, Ar C-5, CH=CH), 122 (ArC-6), 115 (ArC-2, ArC-4), 105 (C-1$\beta^{II,III,IV}$), 98 (C-1$\beta^I$) (C-1$\alpha^I$), 82-53 (21 C of the sugars and Ar—CH$_2$—NH), 68 (CH$_2$—OAr), 33-23 (10 CH$_2$ and 3 CH$_3$CO), 14 (CH$_3$)

Mass Spectrum:
Negative ESI m/z=1125.4 [M−Na]−

2-acetamido-4-O-{2-acetamido-4-O-[2-acetamido-2-deoxy-4-O-(2-deoxy-2-(N-3-(undec-4Z-enyloxy)benzyl)acetamido-β-D-glucopyranosyl)-β-D-glucopyranosyl]-2-deoxy-β-D-glucopyranosyl}-2-deoxy-6-O-sulfo-D-glucopyranose, sodium salt (5)

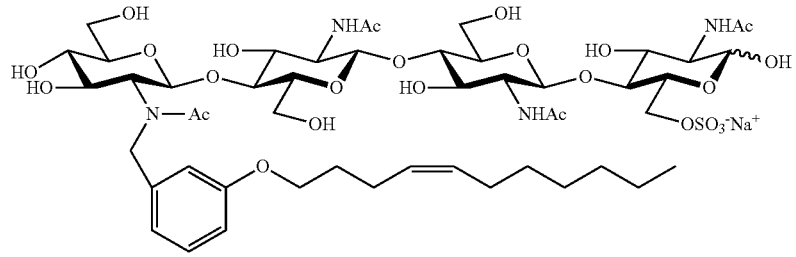

20 mg of sodium hydrogen carbonate and 15 µL of acetic anhydride are added to a solution of 13 mg of 4 (11 µmol) in 0.3 mL of E/M/W (1/1/1). The reaction medium is stirred at room temperature for 12 hours. After concentrating, the residual oil is taken up in E/M/W (1/1/1) and Dowex 50×8-100 H+ resin is added. The mixture is filtered and Amberlite IR120Na+ resin is added to the filtrate. After filtering and concentrating, the product is purified by chromatography in E/M/W (4/1/1). 10 mg of a white solid are thus isolated, i.e. a yield of 77%.

¹H NMR (400 MHz, DMSO-CD₃OD (2/1)) δ (ppm):
7.25-7.18 (2 t, 1H, ArH-5, $J_{5,4}$ 7.8 Hz and $J_{5,6}$ 7.9 Hz), 7.10-6.85 (m, 2H, ArH-2 and ArH-6), 6.82-6.75 (2 d, 1H, Ar H-4), 5.40 (m, 2H, CH=CH), 5.06 (d, 0.6H, H-1α$^I$, $J_{1\alpha,2}$ 3.4 Hz), 4.75-4.35 (m, 3.4H, H-1β$^{I,II,III,IV}$), 4.30-4.05 (m, 2H, H-6a, b$^I$), 4.00-3.30 (m, 25H, other Hs of the sugars and CH₂—OAr), 3.80 (s, 2H, NAc—CH₂Ar), 2.90 (m, 1H, H-2$^{IV}$), 2.23-2.03 (2 m, 4H, CH₂—CH=CH—CH₂), 1.99-1.90 (m, 12H, CH₃CO), 1.80 (tt, 2H, ArO—CH₂—CH₂—CH₂—CH=CH, J 6.9 Hz), 1.35-1.20 (m, 8H, 4 CH₂), 0.87 (m, 3H, CH₃)

¹³C NMR (50 MHz, DMSO-CD₃OD (2/1)) δ (ppm): 176 (CH₃CON), 174-173-173 (3 CH₃CO), 161 (ArC-3), 141 (Ar C-1), 132-130-129-127 (ArC-2, ArC-4, ArC-5, ArC-6, CH=CH), 103 (3 C-1β$^{I,II,IV}$), 100 (C-1β$^I$), 92 (C-1α$^I$), 82-50 (24 C of the sugars, Ar—CH₂—NH and CH₂—OAr), 33-23 (10 CH₂ and 3 CH₃CO), 14 (CH₃)

Mass spectrum: Negative ESI m/z=1067.4 [M−Na]−

2-acetamido-4-O-{2-acetamido-4-O-[2-acetamido-2-deoxy-4-O-(2-deoxy-2-(N-3-(undecanyloxy)benzoyl)amino-β-D-glucopyranosyl)-2-deoxy-β-D-glucopyranosyl]-β-D-glucopyranosyl}-2-deoxy-6-O-sulfo-D-glucopyranose, sodium salt (6)

solution of chloride and 16 mg of sodium hydrogen carbonate are added in eight portions over 24 hours. After concentrating, the residue is purified by placing it in DCM/methanol (5/1) on a column of silica, while diluting it greatly, in order to remove the lipid chain. The elution is then performed with E/M/W (4/1/1). 6.3 mg of a white solid are thus isolated, i.e. a yield of 32%.

¹H NMR (400 MHz, DMSO-CD₃OD (⅓)) δ (ppm): 7.44 (m, 2H, ArH-2 and ArH-6), 7.39 (dd, 1H, ArH-5, $J_{5,4}$≈$J_{5,6}$ 7.9 Hz), 7.10 (ddd, 1H, ArH-4, $J_{4,6}$≈$J_{4,2}$ 2.1 Hz), 5.05 (d, 0.7H, H-1α$^I$, $J_{1\alpha,2}$ 3.0 Hz), 4.70-4.40 (m, 3.3H, H-1β$^{I,II,III,IV}$) 4.22 (m, 1H, H-6a$^I$), 4.10-3.20 (m, 24H, CH₂—OAr and other Hs of the sugar), 2.03-1.99-1.96 (3 s, 9H, CH₃CO), 1.80 (m, 2H, ArO—CH₂—CH₂—CH₂), 1.35-1.25 (m, 8H, 4 CH₂), 0.92 (t, 3H, CH₃, J 6.5 Hz)

Mass spectrum: Negative ESI m/z=1141.5 [M−Na]−

2-acetamido-4-O-{2-acetamido-4-O-[2-acetamido-2-deoxy-4-O-(2-deoxy-2-(N-3-(undec-4Z-ynyloxy)benzoyl)amino-β-D-glucopyranosyl)-β-D-glucopyranosyl]-2-deoxy-β-D-glucopyranosyl}-2-deoxy-6-O-sulfo-o-glucopyranose, sodium salt (7)

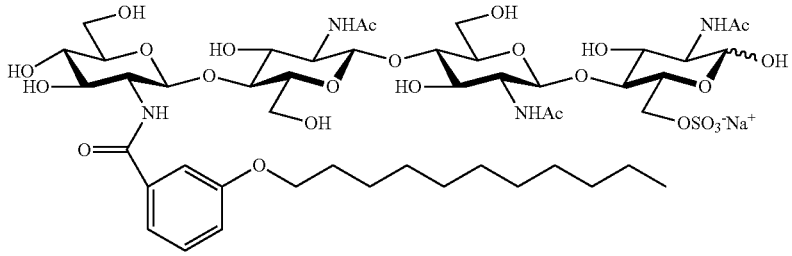

15 mg of CO—IV(NH₂,S) (17 μmol) are dissolved in 100 μL of water and 250 μL of DMF. 6 mg of sodium hydrogen carbonate (71 μmol) and then 25 μL of a solution of 23 in THF at a concentration of 210 mg/mL (17 μmol) are then added. The reaction medium is heated to 60° C. and 200 μL of the

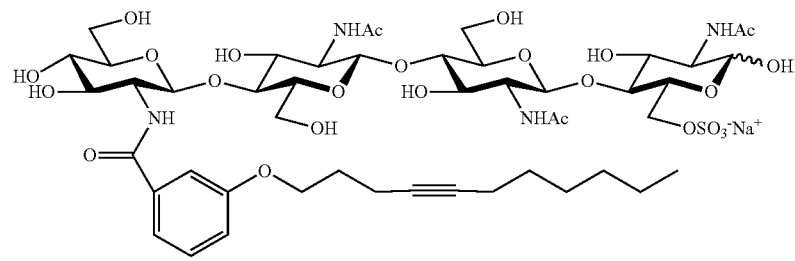

14 mg of CO—IV(NH$_2$,S) (16 µmol) are dissolved in 100 µL of water and 250 µL of DMF. 5 mg of sodium hydrogen carbonate (60 µmol) and then 25 µL of a solution of 27 in THF at a concentration of 190 mg/mL (16 µmol) are then added. The reaction medium is heated to 60° C. and 200 µL of the solution of chloride and 16 mg of sodium hydrogen carbonate are added in eight portions over 24 hours. After concentrating, the residue is purified by placing it in DCM/methanol (5/1) on a column of silica, while diluting it greatly, in order to remove the lipid chain. The elution is then performed with E/M/W (4/1/1). 5.7 mg of expected product are thus isolated in the form of a white solid, i.e. a yield of 31%.

$^1$H NMR (400 MHz, DMSO-CD$_3$OD (½)) δ (ppm): 7.43 (m, 2H, ArH-2 and ArH-6), 7.37 (dd, 1H, ArH-5, J$_{5,4}$ 8.1 Hz and J$_{5,6}$ 8.0 Hz), 7.10 (ddd, 1H, ArH-4, J$_{4,2}$≈J$_{4,6}$ 2.0 Hz), 5.04 (d, 0.7H, H-1α$^I$, J$_{1α,2}$ 3.3 Hz), 4.65-4.59 (2 d, 2H, H-1β$^{II,III}$, J$_{1β,2}$ 8.4 Hz and J$_{1β,2}$ 8.5 Hz), 4.54 (d, 0.3H, H-1β$^I$, J$_{1β,2}$ 7.9 Hz), 4.49 (d, 1H, H-1β$^{IV}$, J$_{1β,2}$ 8.7 Hz), 4.23 (dd, 1H, H-6a$^I$, J$_{6a,6b}$ 11.1 Hz and J$_{6a,5}$ 3.7 Hz), 4.12 (t, 2H, C$\underline{H}_2$—OAr, J 6.2 Hz), 4.10-3.40 (m, 21H, other Hs of the sugars), 2.35-2.13 (2 m, 4H, C$\underline{H}_2$—C≡C—C$\underline{H}_2$), 2.02-1.98-1.96 (3 s, 9H, 3 C$\underline{H}_3$CO), 1.92 (m, 2H, ArO—CH$_2$—C$\underline{H}_2$—CH$_2$), 1.45-1.25 (m, 8H, 4 C$\underline{H}_2$), 0.88 (t, 3H, C$\underline{H}_3$, J 6.7 Hz)

$^{13}$C NMR (62.5 MHz, DMSO-CD$_3$OD (½)) δ (ppm): 173 (3 $\underline{C}$H$_3$CO), 170 (N$\underline{C}$OAr), 158 (ArC-3), 137 (ArC-1), 131 (ArC-5), 121 (ArC-6), 119 (ArC-4), 115 (ArC-2), 103 ($\underline{C}$-1β$^{II,III,IV}$), 96 ($\underline{C}$-1β$^I$), 92 ($\underline{C}$-1α$^I$), 82-50 (20 $\underline{C}$ of the sugars, $\underline{C}$≡$\underline{C}$ and $\underline{C}$H$_2$—OAr), 33-16 (7 $\underline{C}$H$_2$ and 3 $\underline{C}$H$_3$CO), 15 ($\underline{C}$H$_3$)

Mass spectrum:
Negative ESI m/z=1137.1 [M−Na]−

2-acetamido-4-O-{2-acetamido-4-O-[2-acetamido-2-deoxy-4-O-(2-deoxy-2-(N-2-(undec-4Z-enyloxy) benzoyl)amino-β-D-glucopyranosyl)-β-D-glucopyranosyl]-2-deoxy-β-D-glucopyranosyl}-2-deoxy-6-O-sulfo-D-glucopyranose, sodium salt (8)

reaction medium is heated to 60° C. and 105 µL of the solution of chloride and 6 mg of sodium hydrogen carbonate are added in seven portions over 18 hours. After concentrating, the residue is purified by placing it in DCM/methanol (5/1) on a column of silica, while diluting it greatly, in order to remove the lipid chain. The elution is then performed with E/M/W (9/2/1). 6.2 mg of a white solid are thus isolated, i.e. a yield of 48% (but a conversion of only 50%).

$^1$H NMR (400 MHz, DMSO-CD$_3$OD (½)) δ (ppm):
7.99 (dd, 1H, ArH-6, J$_{6,5}$ 7.5 Hz and J$_{6,4}$ 1.8 Hz), 7.55 (ddd, 1H, ArH-4, J$_{4,3}$ 8.3 Hz and J$_{4,5}$ 7.8 Hz), 7.20 (d, 1H, ArH-3), 7.10 (dd, 1H, ArH-5), 5.52 (m, 2H, CH=CH), 5.06 (d, 0.7H, H-1α$^I$, J$_{1α,2}$ 3.0 Hz), 4.70-4.60-4.53 (4 d superimposed, 3.6H, $\underline{H}$-1β$^{I,II,III,IV}$), 4.20-3.40 (m, 25H, other Hs of the sugars and $\underline{CH}_2$—OAr), 2.33-2.11 (2 m, 4H, C$\underline{H}_2$—CH=CH—C$\underline{H}_2$), 2.03-2.01-2.00 (3 s, 9H, 3 C$\underline{H}_3$CO), 2.05 (m, 2H, ArO—CH$_2$—C$\underline{H}_2$—CH$_2$), 1.50-1.20 (m, 8H, 4 C$\underline{H}_2$), 0.94 (t, 3H, C$\underline{H}_3$, J 6.8 Hz)

$^{13}$C NMR (62.5 MHz, DMSO-CD$_3$OD (½)) δ (ppm):
172 (3 $\underline{C}$H$_3$CO), 171 (N$\underline{C}$OAr), 158 (ArC-1), 133 (ArC-4, $\underline{C}$H=$\underline{C}$H), 129 (ArC-6), 122 (ArC-5), 114 (ArC-3), 103 ($\underline{C}$-1β$^{II,III,IV}$), 96 ($\underline{C}$-1β$^I$), 92 ($\underline{C}$-1α$^I$), 82-50 (all the other Cs of the sugars and $\underline{C}$H$_2$OAr), 33-24 (7 $\underline{C}$H$_2$ and 3 $\underline{C}$H$_3$CO), 15 ($\underline{C}$H$_3$)

Mass spectrum:
Negative ESI m/z=1139.5 [M−Na]−

2-acetamido-4-O-{2-acetamido-4-O-[2-acetamido-2-deoxy-4-O-(2-deoxy-2-(N-4-(undec-4Z-enyloxy) benzoyi)amino-β-D-glucopyranosyl)-β-D-glucopyranosyl]-2-deoxy-β-D-glucopyranosyl}-2-deoxy-6-O-sulfo-D-glucopyranose, sodium salt (9)

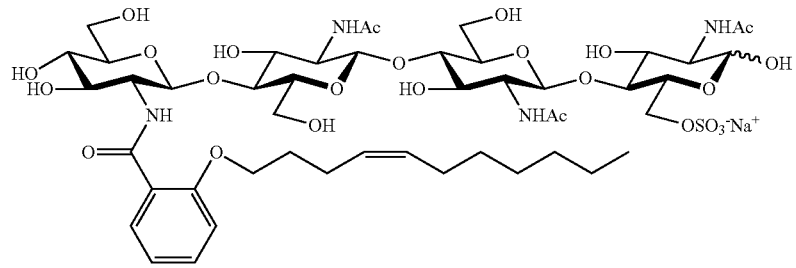

10 mg of CO—IV(NH$_2$,S) (11 µmol) are dissolved in 100 µL of water and 250 µL of DMF. 2 mg of sodium hydrogen carbonate (24 µmol) and then 15 µL of a solution of 31 in THF at a concentration of 115 mg/mL (6 µmol) are then added. The

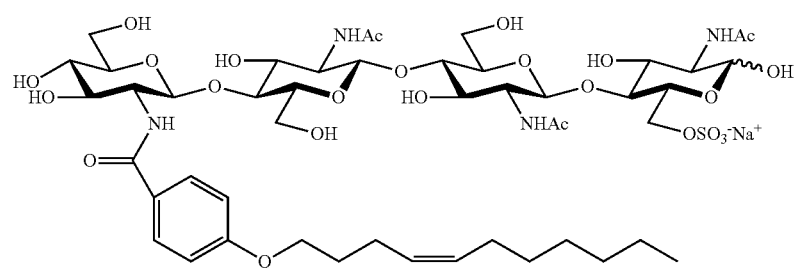

10 mg of CO—IV(NH$_2$,S) (11 µmol) are dissolved in 100 µL of water and 250 µL of DMF. 2 mg of sodium hydrogen carbonate (24 µmol) and then 15 µL of a solution of 35 in THF at a concentration of 115 mg/mL (6 µmol) are then added. The reaction medium is heated to 60° C. and 105 µL of the solution of chloride and 6 mg of sodium hydrogen carbonate are added in seven portions over 17 hours. After concentrating, the residue is purified by placing it in DCM/methanol (5/1) on a column of silica, while diluting it greatly, in order to remove the lipid chain. The elution is then performed with E/M/W (9/2/1). 5.2 mg of a white solid are thus isolated, i.e. a yield of 40% (but a conversion of only 60%).

$^1$H NMR (400 MHz, DMSO-CD$_3$OD (½)) δ (ppm):

7.89 (d, 2H, ArH-2 and ArH-6, $J_{2,3} \approx J_{6,5}$ 8.8 Hz), 7.04 (d, 2H, ArH-3 and ArH-5), 5.48 (m, 2H, CH=CH), 5.05 (d, 0.6H, H-1α$^I$, $J_{1α,2}$ 3.1 Hz), 4.69-4.55-4.50 (4 d superimposed, 3.6H, H-1β$^{I,II,III,IV}$), 4.30-3.40 (m, 23H, other Hs of the sugars), 4.10 (t, CH$_2$—OAr, J 6.3 Hz), 2.28-2.09 (2 m, 4H, CH$_2$—CH=CH—CH$_2$), 2.02-1.99-1.97 (3 s, 9H, 3 CH$_3$CO), 1.89 (m, 2H, ArO—CH$_2$—CH$_2$—CH$_2$), 1.45-1.25 (m, 8 H, 4 CH$_2$), 0.93 (t, 3H, CH$_3$, J=7.0 Hz)

$^{13}$C NMR (62.5 MHz, DMSO-CD$_3$OD (½)) δ (ppm):

172 (3 CH$_3$CO), 169 (NCOAr), 163 (ArC-1), 132-130-129 (ArC-2, ArC-6, CH=CH), 115 (ArC-3, ArC-5), 103 (C-1β$^{II,III,IV}$), 97 (C-1β$^I$), 92 (C-1α$^I$), 83-50 (all the other Cs of the sugars and CH$_2$OAr), 33-23 (7 CH$_2$ and 3 CH$_3$CO), 15 (CH$_3$)

Mass spectrum:

Negative ESI m/z=1139.5 [M−Na]−

2-acetamido-4-O-[2-acetamido-4-O-{2-acetamido-4-O-[2-acetamido-2-deoxy-4-O-(2-deoxy-2-(N-3-(undec-4Z-enyloxy)benzoyl)amino-β-D-glucopyranosyl)-β-D-glucopyranosyl]-2-deoxy-β-D-glucopyranosyl}-2-deoxy-β-D-glucopyranosyl]-2-deoxy-6-O-(-α-L-fucopyranosyl)-D-glucopyranose (10)

various fractions are passed through a Dowex 50×8-100 resin (H$^+$), and then pooled and concentrated. The residue is successively washed with EtOAc (3×1 mL) and then H$_2$O (3×1 mL), and then redissolved in H$_2$O/CH$_3$CN (1/1, 10 mL) by heating to 56° C., and then by sonication. The solution is then freeze-dried, and the expected product is obtained in the form of a white powder (2.5 mg, 28%). The starting material retained on the acid resin is then eluted (2.3 mg, 31%) using aqueous ammonia solution (H$_2$O, 2%).

$^1$H NMR (400 MHz, DMSO-d6/D$_2$O 20/1) δ (ppm):

7.43-7.30 (m, 3H, ArH-2, ArH-6 and ArH-5); 7.05 (m, 1H, ArH-4); 5.45-5.32 (m, 2H, CH=CH); 4.84 (d, 0.8H, $J_{1,2}$=1.9 Hz, H-1α$^I$); 4.66 (d, 0.8H, $J_{1,2}$<1.0 Hz, H-1Fuc-GlcNAcα), 4.65 (d, 0.2H, $J_{1,2}$<1.0 Hz, H-1Fuc-GlcNAcβ), 4.52 (d, H, J=8.5 Hz, H-1β$^{IV}$), 4.45/4.35/4.33 (4d, 4H, J=8.5 Hz, H-1β$^{II-IV}$), 4.42 (d, 0.2H, J=7.0 Hz, H-1β$^I$); 3.99 (t, 2H, J=6.1 Hz, ArOCH$_2$—CH$_2$), 3.88 (dt, 1H, H-5Fuc), 3.78-3.05 (m, 33H, other sugar Hs), 2.17 (dt, 2H, J=6.0 and J=6.8 Hz, CH$_2$—CH=CH), 1.99 (dt, 2H, J=5.9 and J=6.2 Hz, CH=CH—CH$_2$), 1.82/1.81/1.81/1.79 (4s, 12H, 4 COCH$_3$), 1.80-1.72 (m, 2H, ArOCH$_2$—CH$_2$), 1.31-1.15 (m, 8H, 4 CH$_2$), 1.08 (d, 0.6H, $J_{5,6}$=6.9 Hz, H-6Fuc-GlcNAcβ), 1.05 (d, 2.4H, $J_{5,6}$=6.5 Hz, H-6Fuc-GlcNAcα), 0.82 (t, 3H, CH$_3$, J=6.5 Hz).

methyl 3-(undec-4Z-enyloxy)benzoate (15)

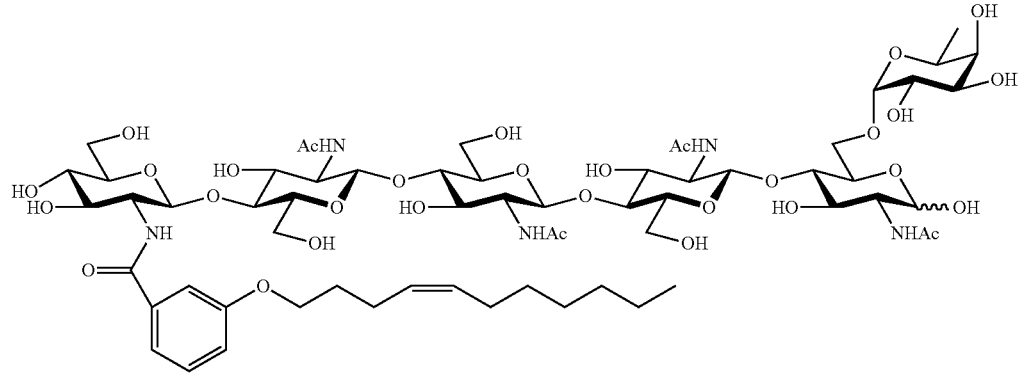

The fucosyl pentamer CO—V(NH$_2$, Fuc) (7.3 mg, 6.4 µmol) is dissolved in H$_2$O (140 µL), followed by addition of DMF (350 µL) and the mixture is brought to 30° C. Dowex 1×2-100 resin (HCO$_3^-$) is then added, followed by addition of a solution (THF, 110 µL) of the acid chloride 19 (6 mg). The reaction mixture is stirred for 24 hours, during which time three further additions of resin and of acid chloride solution are made. The reaction medium is then diluted in H$_2$O/CH$_3$CN (1/1, 2 mL), heated to 56° C., and the supernatant is then filtered through cotton wool. The resin beads and the walls of the flask are extracted several times at 56° C. with H$_2$O/CH$_3$CN (4/1, 7/3, 3/2, 1/1, ⅔, 3/7 and ¼, 2 mL each). The 850 mg of 14 (6.15 mmol) and 900 mg of K$_2$CO$_3$ (6.51 mmol) are added to 1.7 g of 13 (6.07 mmol) in anhydrous DMF (20 mL). After reaction for 4 hours at 90° C., the reaction medium is concentrated, taken up in DCM and then washed with water. 1.87 g of a yellow oil are obtained, and are chromatographed on silica gel in pentane/ethyl acetate (50/1). 1.37 g of a yellow oil are isolated, i.e. a yield of 76%.

$^1$H NMR (250 MHz, CDCl$_3$) δ (ppm):

7.60 (ddd, 1H, ArH-6, $J_{6,5}$ 8.0 Hz and $J_{6,4} \approx J_{6,2}$ 0.5 Hz), 7.52 (dd, 1H, ArH-2, $J_{2,4}$ 3.0 Hz), 7.31 (dd, 1 H, ArH-5, $J_{5,4}$ 8.0 Hz), 7.07 (ddd, 1H, ArH-4), 5.38 (m, 2H, CH=CH), 3.98 (t, 2H, CH$_2$—OAr, J 6.3 Hz), 3.89 (s, 3H, OCH$_3$), 2.22-1.99 (2 m, 4H, CH$_2$—CH=CH—CH$_2$), 1.83 (tt, 2H, ArO—CH$_2$—CH$_2$—CH$_2$—CH=CH, J 6.8 Hz), 1.55-1.20 (m, 8H, 4 CH$_2$), 0.84 (t, 3H, CH$_3$, J 7.5 Hz)

$^{13}$C NMR (62.5 MHz, CDCl$_3$) δ (ppm):
131-129-128 (C-5, CH=CH), 122 (C-6), 120 (C-4), 115 (C-2), 66 (CH$_2$—OAr), 52 (CH$_3$O), 32-22 (7 CH$_2$), 14 (CH$_3$)

Mass spectrum:
Positive ESI m/z=327.2 [M+Na]+
High res. Calc. for C$_{19}$H$_{28}$O$_3$Na: 327.193614, Found: 327.193200
Elemental analysis:

|   | Calc. | Found |
|---|-------|-------|
| C | 74.96 | 74.68 |
| H | 9.27  | 9.37  |
| O | 15.77 | 15.79 |

Infrared (cm$^{-1}$): 2970-2950-2927-2858-1726-1586-1446-1288-1228-756

3-(undec-4Z-enyloxy)benzyl alcohol (16)

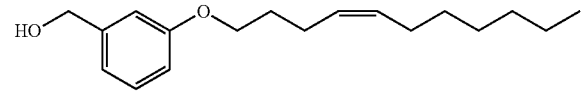

35 mg of lithium aluminum hydride (922 μmol) are added, at 0° C., to 140 mg of 15 (460 μmol) in ether (3 mL). After reaction for 1 hour 30 minutes, the reaction medium is diluted with ether and hydrolyzed with two drops of water. After filtering through Celite, drying over Na$_2$SO$_4$ and concentrating, 127 mg of a colorless oil are isolated, i.e. a yield of 99%.

$^1$H NMR (250 MHz, CDCl$_3$) δ (ppm):
7.18 (dd, 1H, ArH-5, J$_{5,6}$ 8.0 Hz and J$_{5,4}$ 8.3 Hz), 6.84 (m, 2H, ArH-2 and ArH-4), 6.75 (dd, 1H, ArH-4, J$_{4,2}$ 2.9 Hz), 5.32 (m, 2H, CH=CH), 4.58 (s, 2H, CH$_2$OH), 3.89 (t, 2H, CH$_2$—OAr, J 6.3 Hz), 2.16-1.95 (2 m, 4H, CH$_2$—CH=CH—CH$_2$), 1.76 (ft, 2H, ArO—CH$_2$—CH$_2$—CH$_2$—CH=CH, J 6.8 Hz), 1.45-1.18 (m, 8 H, 4 CH$_2$), 0.84 (t, 3H, CH$_3$, J 6.3 Hz)

$^{13}$C NMR (62.5 MHz, CDCl$_3$) δ (ppm):
159 (C-3), 142 (C-1), 131-130-128 (C-5, CH=CH), 119 (C-6), 114 (C-4), 113 (C-2), 67 (CH$_2$—OAr), 65 (CH$_2$OH), 32-23 (7 CH$_2$), 14 (CH$_3$)

Mass spectrum:
Positive ESI m/z=299.2 [M+Na]+
High res. Calc. for C$_{18}$H$_{28}$O$_2$Na: 299.198700, Found: 299.199250
Infrared (cm$^{-1}$): 3329, 3005, 2940, 2925, 2855, 1669, 1602, 1452, 1264

3-(undec-4Z-enyloxy)benzaldehyde (17)

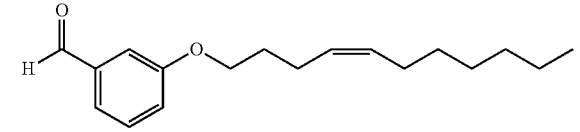

10 mL of anhydrous DCM and then 190 mg of PCC (881 μmol) are added under argon to 120 mg of alcohol 16 (434 μmol) dried by coevaporation with toluene. The reaction is heated to the reflux point of the DCM for 1 hour. After cooling, the reaction medium is diluted with ether and filtered through Florisil. After concentrating, 118 mg of a yellow oil are obtained, i.e. a yield of 99%.

$^1$H NMR (250 MHz, CDCl$_3$) δ (ppm):
9.95 (s, 1H, CHO), 7.42 (m, 2H, ArH-6 and ArH-5), 7.36 (d, 1H, ArH-2, J$_{2,4}$ 2.9 Hz), 7.15 (m, 1H, ArH-4), 5.39 (m, 2H, CH=CH), 3.99 (t, 2H, CH$_2$—OAr, J 6.3 Hz), 2.21-1.99 (2 m, 4H, CH$_2$—CH=CH—CH$_2$), 1.84 (tt, 2H, ArO—CH$_2$—CH$_2$—CH$_2$—CH=CH, J 6.8 Hz), 1.40-1.15 (m, 8H, 4 CH$_2$), 0.84 (t, 3H, CH$_3$, J 6.6 Hz)

$^{13}$C NMR (62.5 MHz, CDCl$_3$) δ (ppm):
192 (CHO), 160 (C-3), 138 (C-1), 131-130-128 (C-5, CH=CH), 123 (C-6), 122 (C-4), 113 (C-2), 67 (CH$_2$—OAr), 52 (CH$_3$O), 32-23 (7 CH$_2$), 14 (CH$_3$)

Mass spectrum:
Chemical ionization (CI) 1% solution in DCM
A fine desorption peak
M+1=275
Infrared (cm$^{-1}$): 3005-2940-2927-2855-2723-1700-1599-1452-1263-787

3-(undec-4Z-enyloxy)benzoic acid (18)

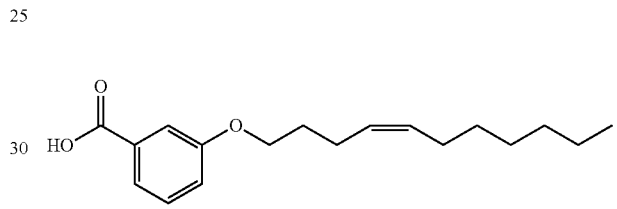

4 mL of 1 N sodium hydroxide solution (4.0 mmol) are added portionwise to 1.14 g of 15 (3.74 mmol) in methanol (30 mL). The solution is refluxed overnight. A further 4 mL of 1 N sodium hydroxide solution are added, and the mixture is refluxed for a further 1 hour 30 minutes. After evaporating off the solvent, the reaction medium is acidified with 0.5 N HCl and extracted with DCM. 1.04 g of a yellow oil are obtained, i.e. a yield of 96%.

$^1$H NMR (200 MHz, CDCl$_3$) δ (ppm):
10.00-9.00 (bd, 1H, CO$_2$H), 7.69 (d, 1H, ArH-6, J$_{6,5}$ 7.8 Hz), 7.60 (d, 1H, ArH-2, J$_{2,4}$ 2.4 Hz), 7.35 (dd, 1H, ArH-5, J$_{5,4}$ 8.3 Hz), 7.14 (dd, 1H, ArH-4), 5.40 (m, 2H, CH=CH), 4.00 (t, 2H, CH$_2$—OAr, J 6.3 Hz), 2.21-2.00 (2 m, 4H, CH$_2$—CH=CH—CH$_2$), 1.85 (tt, 2H, ArO—CH$_2$—CH$_2$—CH$_2$—CH=CH, J 6.8 Hz), 1.35-1.05 (m, 8H, 4 CH$_2$), 0.85 (t, 3H, CH$_3$, J 6.5 Hz)

$^{13}$C NMR (50 MHz, CDCl$_3$) δ (ppm):
172 (CO$_2$H), 159 (C-3), 131-130-130-128 (C-1, C-5, CH=CH), 121-122 (C-4, C-6), 115 (C-2), 67 (CH2—OAr), 32-23 (7 CH$_2$), 14 (CH$_3$)

Mass spectrum:
Negative ESI m/z=289.1 [M-H]
High res. Calc. for C$_{18}$H$_{25}$O$_3$: 289.180370, Found: 289.180730
Elemental analysis:

|   | Calc. | Found |
|---|-------|-------|
| C | 74.45 | 74.29 |
| H | 9.02  | 9.01  |

Infrared (cm$^{-1}$): 2970-2950-2925-2854-1695-1585-1286-757

3-(undec-4Z-enyloxy)benzoyl chloride (19)

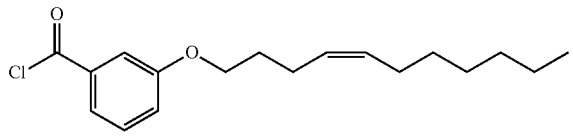

1 mL of oxalyl chloride (11.5 mmol) and two drops of anhydrous DMF are added under argon to 100 mg of toluene-dried 18 (345 µmol) dissolved in 20 mL of anhydrous DCM. The medium is stirred at room temperature for two hours, and then concentrated to give 106 mg of the expected chloride in the form of a yellow oil, i.e. a yield of 99%.

$^1$H NMR (250 MHz, CDCl$_3$) δ (ppm):

7.71 (ddd, 1H, ArH-6, $J_{6,5}$ 8.3 Hz, $J_{6,4}$ 2.4 Hz and $J_{6,2}$ 0.9 Hz), 7.57 (dd, 1H, ArH-2, $J_{2,4}$ 1.6 Hz), 7.39 (dd, 1H, ArH-5, $J_{5,4}$ 8.3 Hz), 7.20 (ddd, 1H, ArH-4), 5.40 (m, 2H, CH=CH), 3.99 (t, 2H, CH$_2$—OAr, J 6.3 Hz), 2.23-2.00 (2 m, 4H, CH$_2$—CH=CH—CH$_2$), 1.85 (tt, 2H, ArO—CH$_2$—CH$_2$—CH$_2$—CH=CH, J 7.0 Hz), 1.28-1.15 (m, 8H, 4 CH$_2$), 0.85 (t, 3H, CH$_3$, J 6.5 Hz)

methyl 3-(undecyloxy)benzoate (21)

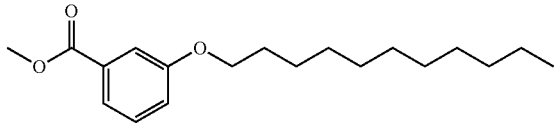

350 mg of 14 (2.30 mmol) and 330 mg of K$_2$CO$_3$ (2.39 mmol) are added to 554 mg of 1-bromoundecane (2.35 mmol) in anhydrous DMF (7 mL). After reaction for 16 hours at 90° C., the reaction medium is concentrated, taken up in DCM and then washed with water. 607 mg of a yellow oil are obtained, and are chromatographed on silica gel in pentane/ethyl acetate (60/1). 579 mg of expected coupling product are isolated in the form of a yellow oil, i.e. a yield of 82%.

$^1$H NMR (200 MHz, CDCl$_3$) δ (ppm):

7.62 (m, 1H, ArH-6), 7.55 (m, 1H, ArH-2), 7.34 (dd, 1H, ArH-5, $J_{5,4}$ 8.1 Hz and $J_{5,6}$ 7.7 Hz), 7.10 (ddd, 1H, ArH-4, $J_{4,6}$ 2.8 Hz and $J_{4,2}$ 0.8 Hz), 4.00 (t, 2H, CH$_2$—OAr, J 6.6 Hz), 3.92 (s, 3H, OCH$_3$), 1.80 (tt, 2H, ArO—CH$_2$—CH$_2$—CH$_2$, J 6.6 Hz and J 6.4 Hz), 1.52-1.20 (m, 16H, 8 CH$_2$), 0.89 (t, 3H, CH$_3$, J 6.7 Hz)

$^{13}$C NMR (62.5 MHz, CDCl$_3$) δ (ppm):

167 (CO$_2$CH$_3$), 159 (C-3), 131 (C-1), 129 (C-5), 122 (C-6), 120 (C-4), 115 (C-2), 68 (CH$_2$—OAr), 52 (CH$_3$O), 32-23 (9 CH$_2$), 14 (CH$_3$)

Mass spectrum:

Positive ESI m/z=329.2 [M+Na]+

High res. Calc. for C$_{19}$H$_{30}$O$_3$Na: 329.209264, Found: 329.207940

Infrared (cm$^{-1}$): 2950-2925-2854-1727-1586-1446-1287-1228-756

3-(undecyloxy)benzoic acid (22)

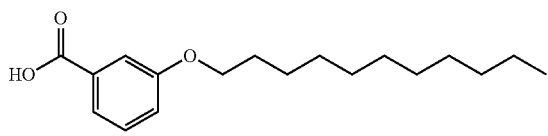

600 µL of 1 N sodium hydroxide solution (600 µmol) are added portionwise to 112 mg of 21 (366 µmol) in methanol (4 mL). The solution is refluxed for two hours. After evaporating off the solvent, the reaction medium is acidified with 0.5 N HCl and extracted with DCM. 107 mg of the expected acid are obtained in the form of a white solid, i.e. a yield of 99%.

$^1$H NMR (250 MHz, CDCl$_3$) δ (ppm):

7.70 (d, 1H, ArH-6, $J_{6,5}$ 7.8 Hz), 7.62 (m, 1H, ArH-2), 7.38 (dd, 1H, ArH-5, $J_{5,4}$ 8.0 Hz), 7.16 (dd, 1H, ArH-4, $J_{4,2}$ 2.1 Hz), 4.02 (t, 2H, CH$_2$—OAr, J 6.5 Hz), 1.99 (tt, 2H, ArO—CH$_2$—CH$_2$—CH$_2$, J 6.6 Hz), 1.55-1.20 (m, 16H, 8 CH$_2$), 0.89 (t, 3H, CH$_3$, J 6.5 Hz)

$^{13}$C NMR (62.5 MHz, CDCl$_3$) δ (ppm):

171 (CO$_2$H), 159 (C-3), 130 (C-1), 129 (C-5), 122 (C-6), 121 (C-4), 115 (C-2), 68 (CH$_2$—OAr), 32-23 (9 CH$_2$), 14 (CH$_3$)

Mass spectrum:

Negative ESI m/z=291.2 [M-H]—

High res. Calc. for C$_{18}$H$_{27}$O$_3$: 291.196020, Found: 291.196560

Infrared (cm$^{-1}$): 2950-2920-2850-2700-2400-1680-1603-1455-1420-1312-1247-757

Melting point: 88° C.

3-(undecanyloxy)benzoyl chloride (23)

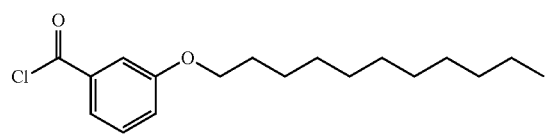

1 mL of oxalyl chloride (11.5 mmol) and two drops of anhydrous DMF are added under argon to 93 mg of toluene-dried acid 22 (318 mid) dissolved in 20 mL of anhydrous DCM. The medium is stirred at room temperature for two hours, and then concentrated to give 99 mg of a yellow oil, i.e. a yield of 99%.

methyl 3-(undec-4-ynyloxy)benzoate (25)

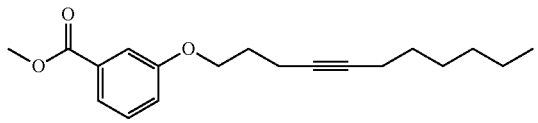

325 mg of 14 (2.14 mmol) and 300 mg of K$_2$CO$_3$ (2.17 mmol) are added to 600 mg of 24 (2.16 mmol) in anhydrous DMF (7 mL). After reaction for 6 hours at 90° C., the reaction medium is concentrated, washed with DCM and then taken up in water. 639 mg of a yellow oil are obtained, and are chromatographed on silica gel in pentane/ethyl acetate (50/1). 429 mg of a yellow oil are isolated, i.e. a yield of 66%.

$^1$H NMR (200 MHz, CDCl$_3$) δ (ppm):

7.63 (m, 1H, ArH-6), 7.57 (m, 1H, ArH-2), 7.31 (dd, 1H, ArH-5, $J_{5,4}$ 8.1 Hz and $J_{5,6}$ 7.8 Hz), 7.11 (ddd, 1H, ArH-4, $J_{4,6}$ 2.4 Hz and $J_{4,2}$ 0.8 Hz), 4.11 (t, 2H, CH$_2$—OAr, J=6.2 Hz), 3.92 (s, 3H, OCH$_3$), 2.39-2.15 (2 m, 4H, CH$_2$—C≡C—CH$_2$), 1.98 (tt, 2H, ArO—CH$_2$—CH$_2$—CH$_2$—C≡C, J 6.5 Hz), 1.52-1.23 (m, 8 H, 4 CH$_2$), 0.88 (t, 3H, CH$_3$, J 6.7 Hz)

$^{13}$C NMR (62.5 MHz, CDCl$_3$) δ (ppm):

167 (CO$_2$CH$_3$), 159 (C-3), 131 (C-1), 129 (C-5), 122 (C-6), 120 (C-4), 115 (C-2), 81-79 (C≡C), 67 (CH$_2$—OAr), 52 (CH$_3$O), 31-15 (7 CH$_2$), 14 (CH$_3$)

Mass spectrum:

Positive ESI m/z=325.1 [M+Na]+

High res. Calc. for C$_{19}$H$_{26}$O$_3$Na: 325.177964, Found: 325.178070

Infrared (cm$^{-1}$): 2950-2931-2857-1726-1586-1446-1288-1228-756

3-(undec-4-ynyloxy)benzoic acid (26)

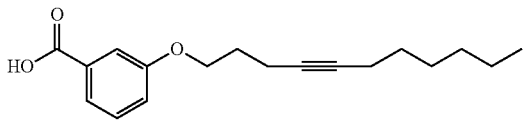

300 µL of 1 N sodium hydroxide solution (300 µmol) are added portionwise to 48 mg of 25 (157 µmol) in methanol (2 mL). The solution is refluxed for 1 hour 30 minutes. After evaporating off the solvent, the reaction medium is acidified with 0.5 N HCl and extracted with DCM. 45 mg of a pale yellow oil are obtained, i.e. a yield of 99%.

$^1$H NMR (250 MHz, CDCl$_3$) δ (ppm):
11.00-10.00 (bd, 1H, CO$_2$H), 7.72 (d, 1H, ArH-6, J$_{6,5}$ 7.7 Hz), 7.64 (m, 1H, ArH-2), 7.38 (dd, 1H, ArH-5, J$_{5,4}$ 8.1 Hz), 7.17 (dd, 1H, ArH-4, J$_{4,2}$ 2.7 Hz), 4.13 (t, 2H, CH$_2$—OAr, J 6.1 Hz), 2.39-2.15 (2 m, 4H, CH$_2$—C≡C—CH$_2$), 1.99 (tt, 2H, ArO—CH$_2$—CH$_2$—CH$_2$—C≡C, J 6.5 Hz), 1.50-1.20 (m, 8H, 4 CH$_2$), 0.88 (t, 3H, CH$_3$, J 6.7 Hz)

$^{13}$C NMR (62.5 MHz, CDCl$_3$) δ (ppm):
172 (CO$_2$H), 159 (C-3), 131 (C-1), 129 (C-5), 123 (C-6), 121 (C-4), 115 (C-2), 81-79 (C≡C), 67 (CH$_2$—OAr), 31-15 (7 CH$_2$), 14 (CH$_3$)

Mass spectrum:
Negative ESI m/z=287.1 [M-H]—
High res. Calc. for C$_{18}$H$_{23}$O$_3$: 287.164719, Found: 287.164820
Infrared (cm$^{-1}$): 2954-2929-2855-2700-2400-1690-1592-1452-1414-1288-1247-756

3-(undec-4Z-ynyloxy)benzoyl chloride (27)

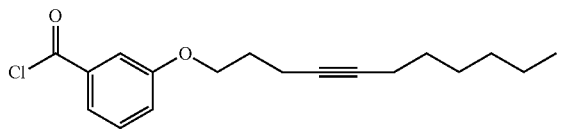

850 µL of oxalyl chloride (9.74 mmol) and two drops of anhydrous DMF are added under argon to 80 mg of toluene-dried acid 26 (278 µmol) dissolved in 17 mL of anhydrous DCM. The medium is stirred at room temperature for two hours, and then concentrated to give 85 mg of a yellow oil, i.e. a yield of 99%.

methyl 2-(undec-4Z-enyloxy)benzoate (29)

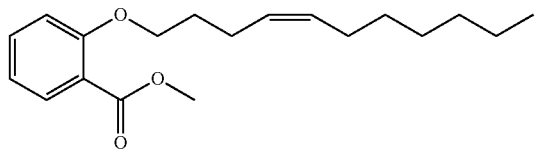

88 mg of 28 (578 µmol) and 77 mg of K$_2$CO$_3$ (557 µmol) are added to 140 mg of 13 (500 µmol) in anhydrous DMF (2 mL). After reaction for 8 hours at 90° C., the reaction medium is concentrated, taken up in DCM and then washed with water. 137 mg of a yellow oil are obtained, and are chromatographed on silica gel in pentane/ethyl acetate (40/1). 100 mg of a yellow oil are isolated, i.e. a yield of 66%.

$^1$H NMR (250 MHz, CDCl$_3$) δ (ppm):
7.79 (dd, 1H, ArH-6, J$_{6,5}$ 8.1 Hz and J$_{6,4}$ 1.9 Hz), 7.43 (ddd, 1H, ArH-4, J$_{4,3}$ 8.5 Hz, J$_{4,5}$ 7.3 Hz), 6.94 (m, 2H, ArH-5 and ArH-3), 5.40 (m, 2H, CH═CH), 4.02 (t, 2H, CH$_2$—OAr, J 6.3 Hz), 3.89 (s, 3H, OCH$_3$), 2.28-2.01 (2 m, 4H, CH$_2$—CH═CH—CH$_2$, J 6.6 Hz), 1.89 (tt, 2H, ArO—CH$_2$—CH$_2$—CH$_2$, J 6.6 Hz), 1.50-1.16 (m, 8H, 4 CH$_2$), 0.86 (t, 3H, CH$_3$, J 6.6 Hz)

$^{13}$C NMR (62.5 MHz, CDCl$_3$) δ (ppm):
167 (C═O), 158 (C-2), 133 (C-4), 131 (CH═CH), 128 (C-6), 120 (C-1), 119 (C-5), 113 (C-3), 68 (CH$_2$—OAr), 52 (CH$_3$O), 32-22 (7 CH$_2$), 14 (CH$_3$)

Mass spectrum:
Positive ESI m/z=327.2 [M+Na]+
High res. Calc. for C$_{19}$H$_{28}$O$_3$Na: 327.193914, Found: 327.192560
Infrared (cm$^{-1}$): 3000-2962-2925-2855-1734-1601-1491-1456-1305-1250-754

2-(undec-4Z-enyloxy)benzoic acid (30)

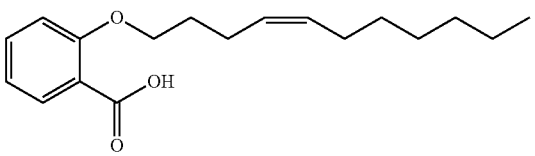

500 µL of 1 N sodium hydroxide solution (500 µmol) are added portionwise to 80 mg of 29 (263 µmol) in methanol (3 mL). The solution is refluxed for 24 hours. After evaporating off the solvent, the reaction medium is acidified with 0.5 N HCl and extracted with DCM. 76 mg of a yellow oil are obtained, i.e. a yield of 99%.

$^1$H NMR (250 MHz, CDCl$_3$) δ (ppm):
12.00-10.00 (bd, 1H, CO$_2$H), 8.16 (dd, 1H, ArH-6, J$_{6,5}$ 7.8 Hz and J$_{6,4}$ 1.9 Hz), 7.54 (ddd, 1H, ArH-4, J$_{4,3}$ 8.4 Hz and J$_{4,5}$ 7.6 Hz), 7.10 (ddd, 1H, ArH-5, J$_{5,3}$ 0.8 Hz), 7.03 (dd, 1H, ArH-3), 5.40 (m, 2H, CH═CH), 4.24 (t, 2H, CH$_2$—OAr, J 6.4 Hz), 2.25 (m, 2H, CH$_2$—CH═CH—CH$_2$), 1.97 (m, 4H, ArO—CH$_2$—CH$_2$—CH$_2$—CH═CH—CH$_2$), 1.35-1.10 (m, 8H, 4 CH$_2$), 0.84 (t, 3H, CH$_3$, J 6.6 Hz)

$^{13}$C NMR (62.5 MHz, CDCl$_3$) δ (ppm):
165 (CO$_2$H), 157 (C-2), 135 (C-4), 134-132 (CH═CH), 127 (C-6), 122 (C-5), 117 (C-1), 112 (C-3), 69 (CH$_2$—OAr), 32-22 (7 CH$_2$), 14 (CH$_3$)

Mass spectrum:
Negative ESI m/z=289.2 [M-H]—
High res. Calc. for C$_{18}$H$_{25}$O$_3$: 289.180370, Found: 289.179060

2-(undec-4Z-enyloxy)benzoyl chloride (31)

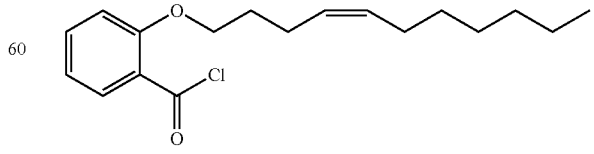

800 µL of oxalyl chloride (9.17 mmol) and two drops of anhydrous DMF are added under argon to 76 mg of toluene-dried acid 30 (262 µmol) dissolved in 15 mL of anhydrous DCM. The medium is stirred at room temperature for two hours and then concentrated to give 80 mg of a yellow oil, i.e. a yield of 99%.

$^1$H NMR (250 MHz, CDCl$_3$) δ (ppm):

7.97 (dd, 1H, ArH-6, J$_{6,5}$ 7.9 Hz and J$_{6,4}$ 1.7 Hz), 7.46 (m, 1H, ArH-4), 6.90 (m, 2H, ArH-5 and ArH-3), 5.30 (m, 2H, CH=CH), 3.95 (t, 2H, CH$_2$—OAr, J 6.3 Hz), 2.20-1.90 (2 m, 4H, CH$_2$—CH=CH—CH$_2$), 1.79 (tt, 2H, ArO—CH$_2$—CH$_2$—CH$_2$—CH=CH, J 6.6 Hz), 1.20-1.09 (m, 8H, 4 CH$_2$), 0.76 (t, 3H, CH$_3$, J 6.7 Hz)

methyl 4-(undec-4Z-enyloxy)benzoate (33)

90 mg of 32 (590 μmol) and 81 mg of K$_2$CO$_3$ (590 μmol) are added to 150 mg of 13 (535 μmol) in anhydrous DMF (2 mL). After reaction for 7 hours at 90° C., the reaction medium is concentrated, taken up in DCM and then washed with water. 163 mg of a yellow oil are obtained, and are chromatographed on silica gel in pentane/ethyl acetate (80/1). 129 mg of the expected coupling product are isolated in the form of a yellow oil, i.e. a yield of 79%.

$^1$H NMR (250 MHz, CDCl$_3$) δ (ppm):

7.97 (d, 2H, ArH-2 and ArH-6, J$_{6,5}$≈J$_{2,3}$ 8.8 Hz), 6.89 (d, 2H, ArH-3 and ArH-5), 5.39 (m, 2H, CH=CH), 3.99 (t, 2H, CH$_2$—OAr, J 6.3 Hz), 3.88 (s, 3H, OCH$_3$), 2.22-2.00 (2 m, 4H, CH$_2$—CH=CH—CH$_2$), 1.84 (tt, 2H, ArO—CH$_2$—CH$_2$—CH$_2$, J 6.8 Hz), 1.40-1.12 (m, 8H, 4 CH$_2$), 0.85 (t, 3H, CH$_3$, J 6.6 Hz)

$^{13}$C NMR (62.5 MHz, CDCl$_3$) δ (ppm): 167 (C=O), 163 (C-4), 131 (C-2 and C-6), 130-128 (CH=CH), 122 (C-1), 114 (C-5 and C-3), 67 (CH$_2$—OAr), 52 (CH$_3$O), 32-23 (7 CH$_2$), 14 (CH$_3$)

Mass spectrum:

Positive ESI m/z=327.2 [M+Na]+

High res. Calc. for C$_{19}$H$_{28}$O$_3$Na: 327.193914, Found: 327.192630

Infrared (cm$^{-1}$): 3000-2962-2925-2855-1720-1607-1511-1435-1279-1254-846

4-(undec-4Z-enyloxy)benzoic acid (34)

550 μL of 1 N sodium hydroxide solution (550 μmol) are added portionwise to 109 mg of 33 (358 μmol) in methanol (4 mL). The solution is refluxed for 20 hours. After evaporating off the solvent, the reaction medium is acidified with 0.5 N HCl and extracted with DCM. 102 mg of a white solid are obtained, i.e. a yield of 98%.

$^1$H NMR (250 MHz, CDCl$_3$) δ (ppm):

12.00-11.00 (bd, 1H, CO$_2$H), 8.07 (d, 2H, ArH-2 and ArH-6, J$_{2,3}$≈J$_{6,5}$ 8.5 Hz), 6.94 (d, 2H, ArH-3 and ArH-5), 5.42 (m, 2H, CH=CH), 4.03 (t, 2H, CH$_2$—OAr, J 6.3 Hz), 2.26-2.03 (2 m, 4H, CH$_2$—CH=CH—CH$_2$), 1.88 (tt, 2H, ArO—CH$_2$—CH$_2$—CH$_2$, J 6.8 Hz), 1.40-1.10 (m, 8H, 4 CH$_2$), 0.89 (t, 3H, CH$_3$, J 6.6 Hz)

$^{13}$C NMR (62.5 MHz, CDCl$_3$) δ (ppm):

172 (CO$_2$H), 164 (C-4), 132 (C-2 and C-6), 131-128 (CH=CH), 121 (C-1), 114 (C-3 and C-5), 67 (CH$_2$—OAr), 32-22 (7 CH$_2$), 14 (CH$_3$)

Mass spectrum:

Negative ESI m/z=289.2 [M-H]—

High res. Calc. for C$_{18}$H$_{25}$O$_3$: 289.180370, Found: 289.178710

4-(undec-4Z-enyloxy)benzoyl chloride (35)

1 mL of oxalyl chloride (11.5 mmol) and two drops of anhydrous DMF are added under argon to 101 mg of toluene-dried acid 34 (348 μmol) dissolved in 18 mL of anhydrous DCM. The medium is stirred at room temperature for two hours and then concentrated to give 107 mg of a yellow oil, i.e. a yield of 99%.

$^1$H NMR (250 MHz, CDCl$_3$) δ (ppm):

7.96 (d, 2H, ArH-2 and ArH-6, J$_{2,3}$≈J$_{6,5}$ 8.7 Hz), 6.99 (d, 2H, ArH-3 and ArH-5), 5.43 (m, 2H, CH=CH), 4.10 (t, 2H, CH$_2$—OAr, J 6.3 Hz), 2.27-2.03 (2 m, 4H, CH$_2$—CH=CH—CH$_2$), 1.91 (tt, 2H, ArO—CH$_2$—CH$_2$—CH$_2$, J 6.7 Hz), 1.35-1.12 (m, 8H, 4 CH$_2$), 0.89 (t, 3H, CH$_3$, J 6.6 Hz)

The invention claimed is:

1. A compound of formula (I)

(I)

in which n represents 1, 2 or 3;

A represents a substituent selected from the group consisting of —C(O)—, —C(S)—, and —CH$_2$—;

B is selected from the group consisting of a biphenylene;

this group optionally being substituted with one or two substituents independently selected from the group consisting of halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;

C represents a substituent selected from the group consisting of —O—, —S—, —CH$_2$—, and CH—(C$_1$-C$_6$-alkyl);

D represents a linear or branched, saturated or unsaturated hydrocarbon-based chain containing from 2 to 20 carbon atoms;

E and G represent, independently of each other, a substituent selected from the group consisting of H, OH, OC(O)CH$_3$ and NHC(O)CH$_3$;

R$^1$ represents a substituent selected from the group consisting of H, C$_{1-6}$-alkyl, C(O)H and C(O)CH$_3$;

R$^2$, R$^3$, R$^6$, R$^{14}$, R$^{15}$, and R$^{16}$ represent, independently of each other, a substituent selected from the group consisting of H, C$_{1-6}$-alkyl, C(O)C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

R$^4$ represents a substituent selected from the group consisting of H, C$_{1-6}$-alkyl and R$^{21}$;

R$^5$ represents a substituent selected from the group consisting of H, C$_{1-6}$-alkyl, fucosyl and R$^{22}$;

R$^7$ represents a substituent selected from the group consisting of H, C$_{1-6}$-alkyl, arabinosyl and R$^{23}$;

R$^8$ represents a substituent selected from the group consisting of H, C$_{1-6}$-alkyl, fucosyl, methylfucosyl, sulfofucosyl, acetylfucosyl, arabinosyl, SO$_3$H, SO$_3$Li, SO$_3$Na, SO$_3$K, SO$_3$N(C$_{1-8}$alkyl)$_4$ and R$^{24}$;

R$^9$ represents a substituent selected from the group consisting of H, C$_{1-6}$-alkyl, mannose, glycerol and R$^{25}$;

R$^{21}$, R$^{22}$, R$^{23}$, R$^{24}$ and R$^{25}$ represent, independently of each other, a substituent selected from the group consisting of C(O)C$_{1-6}$-alkyl, —C(S)C$_{1-6}$-alkyl, —C(O)OC$_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

and the possible geometrical or optical isomers, enantiomers or diastereoisomers, tautomers, salts, N-oxides, sulfoxides, sulfones, and metal or metalloid complexes thereof that are agriculturally acceptable.

2. The compound of formula (I) of claim 1 wherein:
n represents 2 or 3;
A is selected from the group consisting of —C(O)— and —CH$_2$—;
E and G represent NHC(O)CH$_3$;
R$^1$ is selected from the group consisting of H, CH$_3$ and C(O)CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$Li, SO$_3$Na, SO$_3$K, SO$_3$N(C$_{1-8}$-alkyl)$_4$, fucosyl and methylfucosyl.

3. The compound of claim 2 wherein D represents a linear, saturated or unsaturated hydrocarbon-based chain containing from 3 to 17 carbon atoms.

4. The compound of claim 1 wherein A is —C(O)—.

5. The compound of claim 4 wherein:
n represents 2 or 3;
E and G represent NHC(O)CH$_3$;
R$^1$ is selected from the group consisting of H and CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$Li, SO$_3$Na, SO$_3$K, SO$_3$N(C$_{1-8}$-alkyl)$_4$, fucosyl and methylfucosyl.

6. The compound of claim 5 wherein D represents a linear, saturated or unsaturated hydrocarbon-based chain containing from 3 to 17 carbon atoms.

7. The compound of claim 1 wherein A is —CH$_2$—.

8. The compound of claim 7 wherein
n represents 2 or 3;
E and G represent NHC(O)CH$_3$;
R$^1$ is selected from the group consisting of H and C(O)CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$Li, SO$_3$Na, SO$_3$K, SO$_3$N(C$_{1-8}$-alkyl)$_4$, fucosyl and methylfucosyl.

9. The compound of claim 8 wherein D represents a linear, saturated or unsaturated hydrocarbon-based chain containing from 3 to 17 carbon atoms.

10. The compound of claim 9 wherein C represents —O—.

11. The compound of claim 1 wherein C represents —O—.

12. The compound of claim 11 wherein:
n represents 2 or 3;
A is selected from the group consisting of —C(O)— and —CH$_2$—;
E and G represent NHC(O)CH$_3$;
R$^1$ is selected from the group consisting of H, CH$_3$ and C(O)CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$Li, SO$_3$Na, SO$_3$K, SO$_3$N(C$_{1-8}$-alkyl)$_4$, fucosyl and methylfucosyl.

13. The compound of claim 12 wherein D represents a linear, saturated or unsaturated hydrocarbon-based chain containing from 3 to 17 carbon atoms.

14. The compound of claim 1 wherein A is —C(O)— and C is —O—.

15. The compound of claim 14 wherein:
n represents 2 or 3;
E and G represent NHC(O)CH$_3$;
R$^1$ is selected from the group consisting of H and CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$Li, SO$_3$Na, SO$_3$K, SO$_3$N(C$_{1-8}$-alkyl)$_4$, fucosyl and methylfucosyl.

16. The compound of claim 15 wherein D represents a linear, saturated or unsaturated hydrocarbon-based chain containing from 3 to 17 carbon atoms.

17. The compound of claim 1 wherein A is —CH$_2$— and C is —O—.

18. The compound of claim 17 wherein:
n represents 2 or 3;
E and G represent NHC(O)CH$_3$;
R$^1$ is selected from the group consisting of H and C(O)CH$_3$;
R$^2$, R$^3$, R$^5$, R$^6$, R$^7$ and R$^9$ represent H;
R$^4$ is selected from the group consisting of H, C(O)CH$_3$ and C(O)NH$_2$; and
R$^8$ is selected from the group consisting of H, SO$_3$H, SO$_3$L$_1$, SO$_3$Na, SO$_3$K, SO$_3$N(C$_{1-8}$alkyl)$_4$, fucosyl and methylfucosyl.

19. The compound of claim 18 wherein D represents a linear, saturated or unsaturated hydrocarbon-based chain containing from 3 to 17 carbon atoms.

20. The compound of claim 1, having at least one of the following characteristics:
n=2 or 3;
A is selected from the group consisting of —C(O)— and —CH$_2$—;
C represents —O—;
E and G represent NHC(O)CH$_3$;

$R^1$ is selected from the group consisting of H and C(O)CH$_3$;

$R^2$, $R^3$, $R^5$, $R^6$, $R^7$ and $R^9$ represent a hydrogen atom;

$R^4$ represents a substituent selected from the group consisting of H, C(O)CH$_3$ and C(O)NH$_2$;

$R^8$ represents a substituent selected from the group consisting of H, fucosyl, methylfucosyl, sulfofucosyl, acetylfucosyl, arabinosyl, SO$_3$H, SO$_3$L$_1$, SO$_3$Na, SO$_3$K and SO$_3$N(C$_{1-8}$alkyl)$_4$.

21. The compound of claim 1 wherein:

n=2 or 3;

A is selected from the group consisting of —C(O)— and —CH$_2$—;

C represents —O—;

E and G represent NHC(O)CH$_3$;

$R^1$ is selected from the group consisting of H and C(O)CH$_3$;

$R^2$, $R^3$, $R^5$, $R^6$, $R^7$ and $R^9$ represent a hydrogen atom;

$R^4$ represents a substituent selected from the group consisting of H, C(O)CH$_3$ and C(O)NH$_2$; and $R^8$ represents a substituent selected from the group consisting of H, fucosyl, methylfucosyl, sulfofucosyl, acetylfucosyl, arabinosyl, SO$_3$H, SO$_3$Li, SO$_3$Na, SO$_3$K and SO$_3$N(C$_{1-8}$-alkyl)$_4$.

22. The compound of claim 1 wherein $R^8$ is selected from the group consisting of H, SO$_3$H, SO$_3$Li, SO$_3$Na, SO$_3$K, SO$_3$N(C$_{1-8}$-alkyl)$_4$ and a substituent of formula:

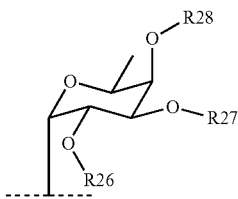

wherein $R^{26}$ K represents a substituent selected from the group consisting of H and CH$_3$; and $R^{27}$ and $R^{28}$ represent, independently of each other, a substituent selected from the group consisting of H, C(O)CH$_3$, SO$_3$H, SO$_3$Li, SO$_3$Na, SO$_3$K and SO$_3$N(C$_{1-8}$-alkyl)$_4$.

23. The compound of claim 22 wherein $R^{26}$, $R^{27}$ and $R^{28}$ each represents a hydrogen atom.

24. The compound of claim 1 wherein D represents a linear, saturated or unsaturated hydrocarbon-based chain containing from 7 to 15 carbon atoms.

25. The compound as claimed in claim 1, for which D represents a hydrocarbon-based chain according to one of the formulae represented below

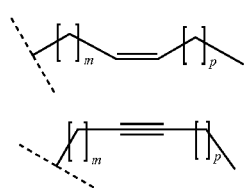

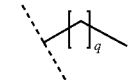

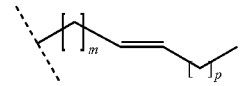

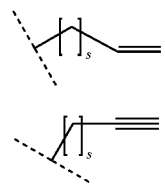

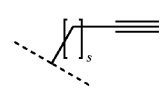

wherein m=1 to 12 p=0 to 11 q=6 to 14 s=5 to 13 with m+p≦12 and m+p≧4.

26. The compound of claim 1 wherein D represents a hydrocarbon-based chain according to one of the formulae represented below

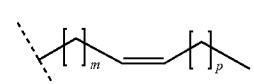

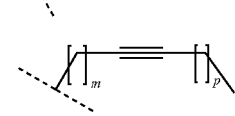

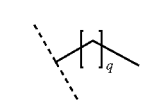

in which m=1 to 12 p=0 to 11 q=6 to 14 with m+p≦12 and m+p≧4.

27. The compound of claim 1 wherein D represents a linear hydrocarbon-based chain comprising 11 carbon atoms that is saturated, or unsaturated between carbon atoms 4 and 5.

28. The compound of claim 1 used as a nodulation factor for a plant.

29. The nodulation factor of claim 28 wherein said plant is a legume.

30. The nodulation factor of claim 29 wherein said legume is soybean, pea, horse bean, groundnut, bean, lupin, alfalfa or clover.

31. The compound of claim 1 used as a plant growth stimulation factor.

32. A process for treating seeds, comprising applying thereto, alone or in combination with other active molecules, one or more compound(s) as defined in claim 1.

* * * * *